US009287219B2

(12) United States Patent
Del Signore et al.

(10) Patent No.: US 9,287,219 B2
(45) Date of Patent: Mar. 15, 2016

(54) RADIATION-BLOCKING STRUCTURES

(71) Applicant: Silicon Laboratories Inc., Austin, TX (US)

(72) Inventors: Bruce P. Del Signore, Hollis, NH (US); John O'Connell, Mallow (IE)

(73) Assignee: Silicon Laboratories Inc., Austin, TX (US)

( * ) Notice: Subject to any disclaimer, the term of this patent is extended or adjusted under 35 U.S.C. 154(b) by 443 days.

(21) Appl. No.: 13/829,998

(22) Filed: Mar. 14, 2013

(65) Prior Publication Data
US 2014/0026653 A1 Jan. 30, 2014

Related U.S. Application Data

(63) Continuation-in-part of application No. 13/557,820, filed on Jul. 25, 2012.

(51) Int. Cl.
*H01L 23/552* (2006.01)
*G01N 27/22* (2006.01)
*G01D 5/24* (2006.01)
*G01D 11/24* (2006.01)

(52) U.S. Cl.
CPC .............. *H01L 23/552* (2013.01); *G01D 5/24* (2013.01); *G01N 27/223* (2013.01); *G01D 11/245* (2013.01); *H01L 2924/0002* (2013.01)

(58) Field of Classification Search
CPC ....................... H01L 23/552; G01N 27/223
See application file for complete search history.

(56) References Cited

U.S. PATENT DOCUMENTS

| 3,826,979 | A | 7/1974 | Steinmann |
| 4,571,543 | A | 2/1986 | Raymond et al. |
| 4,728,882 | A | 3/1988 | Stanbro et al. |
| 4,845,421 | A | 7/1989 | Howarth et al. |
| 5,801,307 | A | 9/1998 | Netzer |
| 6,249,130 | B1 | 6/2001 | Greer |
| 6,373,263 | B1 | 4/2002 | Netzer |
| 6,388,453 | B1 | 5/2002 | Greer |
| 6,842,018 | B2 | 1/2005 | McIntosh |

(Continued)

FOREIGN PATENT DOCUMENTS

EP 2278310 A1 1/2011

OTHER PUBLICATIONS

Gerwen et al., "Nanoscaled Interdigitated Electrode Arrays for Biochemical Sensors", International Conference on Solid State and Actuators, Jun. 1997, 4 pgs.

(Continued)

*Primary Examiner* — Lisa Caputo
*Assistant Examiner* — Punam Roy
(74) *Attorney, Agent, or Firm* — Egan, Peterman, Enders & Huston LLP.

(57) ABSTRACT

Stacked layers of non-continuous opaque layer structures are disclosed herein that may be configured to block radiation such as visible light or other forms of light, while at the same time allowing penetration of ambient gases. In one example, such non-continuous opaque layer structures may be configured as stacked non-continuous metal layer structures that together fully block penetration of radiation while at the same provide sufficient open spaces between and/or within the metal layer segments of a given integrated circuit layer to meet maximum metal spacing rules. In another example, such non-continuous opaque layer structures may be configured as capacitive structures.

19 Claims, 17 Drawing Sheets

(56) References Cited

U.S. PATENT DOCUMENTS

| | | | |
|---|---|---|---|
| 7,554,134 | B2 | 6/2009 | Cummins |
| 7,667,290 | B2 | 2/2010 | Ido et al. |
| 7,728,410 | B2 | 6/2010 | Nakanishi |
| 7,864,063 | B2 | 1/2011 | Rienecker et al. |
| 8,007,167 | B2 | 8/2011 | Cummins |
| 2001/0017053 | A1 | 8/2001 | Rynhart et al. |
| 2003/0091355 | A1 | 5/2003 | Jeschonek et al. |
| 2004/0114075 | A1 | 6/2004 | Iwasa |
| 2008/0309352 | A1 | 12/2008 | Bae et al. |
| 2009/0141767 | A1 | 6/2009 | Cummins et al. |
| 2010/0307238 | A1 | 12/2010 | Van Popta et al. |
| 2012/0035875 | A1 | 2/2012 | Gordon et al. |
| 2012/0234079 | A1 | 9/2012 | Humbert et al. |
| 2013/0139587 | A1 | 6/2013 | LeNeel et al. |
| 2013/0160554 | A1* | 6/2013 | Chen et al. ............... 73/632 |

OTHER PUBLICATIONS

Cummins et al., "Sensor for Measuring High Humidity Conditions And/Or Condensation", U.S. Appl. No. 13/557,739, Filed Jul. 25, 2012, 22 pgs.

Kummer et al., "Configurable Electrodes for Capacitive-Type Sensors And Chemical Sensors", IEEE Sensors Journal, vol. 6, No. 1, Feb. 2006, 8 pgs.

O'Connell, "Capacitive Sensor Comprising Differing Unit Cell Structures", U.S. Appl. No. 13/557,820, Filed Jul. 25, 2012, 27 pgs.

Kummer et al., "Tuning Sensitivity And Selectivity Of Complementary Metal Oxide Semiconductor Based Capacitive Chemical Microsensors", Analytical Chemistry, vol. 76, No. 9, May 1, 2004, 8 pgs.

Oprea et al., "Integrated Temperature, Humidity And Gas Sensors On Flexible Substrates For Low Power Applications", IEEE Sensors, 2007, 4 pgs.

Laconte, et al., "High Sensitivity Capacitive Humidity Sensor Using 3 Layer Patterned Polyimide Sensing Film", IEEE, 2003, 6 pgs.

Mamishev et al., "Assessment Of Performance Of Fringing Electric Field Sensor Arrays", IEEE, 2002, 4 pgs.

Patel et al, "Novel Technique for Measuring Through Plane Modulus In Thin Polymer Films", IEEE, 1998, 4 pgs.

Lofren et al., "Low Power Humidity Sensor For RFID Applications", Multi Material Micro Manufacture, 2008, 4 pgs.

Koll et al., "Discrimination Of Volatile Organic Compounds Using CMOS Capacitive Chemical Microsensors With Thickness Adjusted Coating", SPIE Conference on Smart Electronics and MEMS, vol. 3673, 1999, 10 pgs.

Li et al., "Monolithic CMOS Multi Transducer Gas Sensor Microsystem For Organic And Inorganic Analytes", ScienceDirect, Sensors and Actuators B 126, 2007, 10 pgs.

Chinnam, "Capacitive pH Sensors Using pH Sensitive Polymer", Department of Physics, Chemistry and Biology, Master Thesis, 2009, 56 pgs.

* cited by examiner

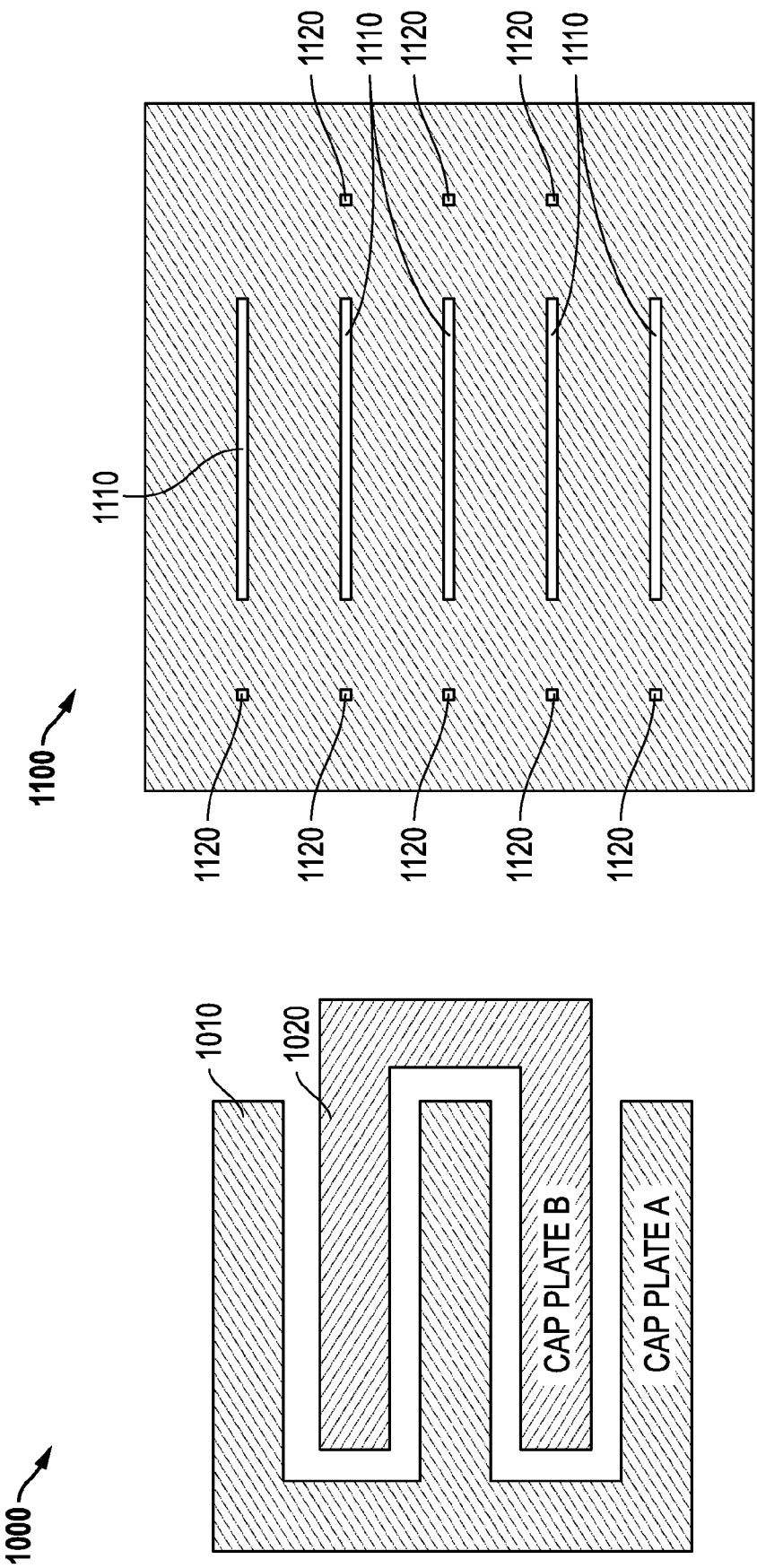

RADIATION-BLOCKING STRUCTURES

This application is a continuation-in-part of co-pending U.S. patent application Ser. No. 13/557,820 filed on Jul. 25, 2012, which is entitled "Capacitive Sensor Comprising Differing Unit Cell Structures" the disclosure of which is incorporated herein by reference.

RELATED APPLICATIONS

This application is related to U.S. patent application Ser. No. 13/557,739, filed Jul. 25, 2012, and entitled "SENSOR FOR MEASURING HIGH HUMIDITY CONDITIONS AND/OR CONDENSATION"; the disclosure of which is expressly incorporated by reference herein in its entirety.

TECHNICAL FIELD OF THE INVENTION

The techniques disclosed herein relate to radiation-blocking structures, and more particularly to radiation-blocking structures that include multiple stacked layer structures that are opaque to incident radiation. The techniques disclosed herein also relate to capacitive sensors, and more particularly capacitive sensors utilized for gas (including humidity) concentration measurements.

BACKGROUND

A wide variety of types of sensors are utilized to measure ambient air conditions such as gas concentrations and relative humidity levels. A capacitive sensor is one known sensor type for measuring gas or humidity concentrations (or other analytes as sensors are not limited to gas and humidity). FIG. 1 illustrates one known technique for forming a capacitive sensor 100. As shown in the FIG. 1 cross-section, sensor electrodes 102, 104 and 106 may be formed on a substrate 101 to form the "fingers" of an interdigitated capacitive structure. It will be recognized that the capacitive structure may be formed by many electrodes arranged as shown in FIG. 1. Capacitance measurements obtained between the electrodes may be utilized to determine gas or relative humidity levels. Sensor electrodes may be any of a wide variety of conductive materials. Substrate 101 may be any of a wide variety of substrates and may be in one non-limiting example a semiconductor substrate that includes a wide variety of integrated circuit layers (not shown) as is known in the art. For example, U.S. Pat. No. 8,007,167 to Cummins, the disclosure of which is expressly incorporated herein by reference, provides a capacitive sensor formed on an integrated circuit substrate. The sensor electrodes may be covered by a passivation layer 103 and further overlayed with a sensing layer 105. Alternatively, sensing layer 105 may be utilized without the inclusion of a passivation layer 103. In operation, the sensing layer 105 is exposed to the ambient conditions under which a measurement is desired. Thus, at least a portion of the upper surface of the sensing layer 105 may be an air/dielectric layer interface and layer 105 may be considered an ambient condition sensitive layer. Typically the concentration in the ambient air of the analyte being measured impacts the dielectric constant of the sensing layer as differing concentrations in the ambient air will impact the amount of ingress of the analyte into the sensor dielectric material. By measuring the capacitance between the electrodes the gas or relative humidity concentrations in the ambient air may be inferred. As shown in FIG. 1, the electric fields between the electrodes may include fields 110a contained in the passivation layer 103, fields 110b which pass in part through the sensing layer 105, and other parasitic fields (not shown). In operation, the changes in the dielectric constant of the sensing layer are the changes utilized to detect the ambient gas or relative humidity conditions. However, all of the various components of the capacitive measurement may be impacted by temperature changes, chemical contaminants, physical contaminants, etc., thus impacting the accuracy of the detection of the ambient conditions.

It would be desirable to provide an improved capacitive sensor structure and method of utilizing such structures.

Capacitive sensors are typically provided in a package with an opening defined in the package that is provided for allowing ingress of ambient air or other gas into the package. Such open packages do not provide the same level of protection from the environment for the enclosed circuitry as do conventional closed package configurations that contain other types of circuitry.

SUMMARY OF THE INVENTION

In one exemplary, non-limiting embodiment, a sensor system may include two differing capacitive sensor unit cell structures. In one embodiment, the sensor system may be a gas and/or relative humidity sensor. A first unit cell structure is constructed such that its capacitance measurement is dependent upon capacitance effects that substantially do not extend to the upper reaches of the sensor's gas/humidity sensitive layer and a second unit cell structure is constructed such that its capacitance measurement is dependent upon electric field effects that extend substantially beyond the electric fields of the first unit cell. The capacitance associated with the electric fields in the mid and/or upper regions of the gas/humidity sensitive layer may then be obtained to a first order by subtracting the capacitance of the first unit cell from the capacitance of the second unit cell. By subtracting the capacitance, a capacitance associated with the capacitance of the electric fields of the layer (or portion of layer) of interest may be approximated while minimizing the effects of other layers, parasitic capacitances, substrate interfaces, the substrate and other stray capacitances. In one embodiment, the electric fields of the first unit cell structure may be confined predominately to layers that do not include the gas/humidity sensitive layer. By subtracting the capacitance, a capacitance associated with the capacitance of the electric fields in the layer of interest (the layer sensitive to a gas or humidity) may be approximated while minimizing the effects of other layers and capacitances. In other embodiments, the number of layers may be minimized such that the electric fields of the second unit cell extend into the gas/humidity sensitive layer but the extent into the gas/humidity layer is to a lesser degree than that the of the first unit cell structure. In such embodiments the subtraction process allows for an isolation of the capacitance effects in the portion of the gas/humidity sensitive layer that is of most interest.

In one exemplary, non-limiting embodiment, a gas and/or humidity sensor is provided in which a capacitive sensor configuration is utilized. The sensor may be comprised of one or more first unit cells and one or more second unit cells. The first unit cell may be constructed to be different from the second unit cell. Moreover, the configuration of the unit cells is such that one unit cell may include capacitance effects of at least a first portion of the gas and/or humidity sensitive layer and other surrounding capacitance effects while the other unit cell includes effects of (1) either none of the gas and/or humidity sensitive layer or smaller portion than the first portion of the gas and/or humidity sensitive layer and (2) the other surrounding capacitance effects. By utilizing measurements from both unit cells, the capacitance effects of the gas and/or humidity sensitive layer (or the most relevant portion of the gas and/or humidity sensitive layer) may be substantially isolated from the effects of the other surrounding capacitance effects. In one exemplary, non-limiting embodiment the utilization of measurements of both unit cells may include a capacitance subtraction process. In one exemplary, non-limiting embodiment the unit cells differ in their periodicity.

In one embodiment, a capacitive gas sensor comprising a gas sensitive material is provided. The gas sensor may be configured to allow the exposure of the gas sensitive material to a gas. A first capacitive sensor cell having first capacitor electrodes is also provided. The first capacitor electrodes have a first set of dimensions, the first capacitive sensor cell being electrically coupled to a first portion of the gas sensitive material. A second capacitive sensor cell having second capacitor electrodes is also provided. The second capacitor electrodes have a second set of dimensions, the second set of dimensions being different from the first set of dimensions, the second capacitive sensor being electrically coupled to a second portion of the gas sensitive material. The second set of dimensions are configured in relation to the first set of dimensions such that electric fields of the second capacitor electrodes extend proportionally further into gas sensitive material than electric fields of the first capacitor electrodes, wherein a combination of the detected capacitance of the first capacitive sensor cell and the second capacitive sensor cell is utilized to obtain a gas sensor measurement.

In yet another embodiment, a method of forming a gas sensor is described. The method may comprise providing a gas sensitive material, the gas sensitive material provided to allow for exposure of the gas sensitive material to a gas. The method may further comprise providing a first set of capacitor electrodes, the first set of capacitor electrodes having a first set of dimensions and providing a second set of capacitor electrodes, the second capacitor electrodes having a second set of dimensions, the second set of dimensions being different from the first set of dimensions. The method further comprises configuring the second set of dimensions to provide proportionally more capacitor electric fields of the second set of capacitor electrodes within the gas sensitive material than the electric fields of the first set of capacitor electrodes and configuring the gas sensor to utilize a combination of the detected capacitance of the first capacitor electrodes and the second capacitor electrodes to obtain a gas sensor measurement.

In yet another embodiment, stacked layers of non-continuous opaque layer structures may be configured to block radiation such as visible light or other forms of light, while at the same time allowing penetration of ambient gases. In this regard, at least two stacked opaque (e.g., metal) layer structures may be configured in one embodiment to block radiation received at a low incident angle so that it cannot penetrate beyond the stacked combination of the two opaque layer structures. In this regard, a stacked radiation-blocking structure may be configured with non-continuous layer structures that are composed of material/s that are opaque to one or more given types or bands of radiation, i.e., that are opaque to, and non-transmissive of, the given type/s or band/s of radiation to be blocked. Such non-continuous opaque layer structures may be configured in one embodiment as stacked non-continuous metal layer structures that together fully block penetration of radiation while at the same time provide sufficient open spaces between and/or within the metal layer segments of a given integrated circuit layer to meet maximum metal spacing rules. Such non-continuous opaque layer structures may be configured in another embodiment as capacitive structures as described further herein.

In one particular exemplary embodiment disclosed herein, a capacitive structure may be provided for an integrated circuit device (e.g., silicon chip) that achieves basic radiation blocking for underlying circuitry by ensuring sufficient metal overlap of at least two stacked metal layers of the capacitive structure. The disclosed radiation-blocking capacitive structure may be advantageously implemented in one example configuration in a position over active circuitry to at least partially or completely block radiation present above the capacitive structure from penetrating through the capacitive structure down to active circuitry that is located in regions of a packaged integrated circuit device that are exposed to the environment, e.g., such as active circuitry located beneath an opening defined in an integrated circuit package to allow ingress of ambient air or other gas from the surrounding environment into the package. However, the disclosed radiation blocking capacitive structures may be implemented with any other integrated circuit configuration to block radiation from penetrating to underlying layers of the integrated circuit. In one exemplary embodiment, such a radiation blocking capacitive structure may be configured to prevent one or more types of electromagnetic radiation (e.g., such as visible light like sunlight and artificial light, X-ray radiation, ultraviolet radiation, infrared radiation, etc.) from penetrating deep into the active region of a silicon chip integrated circuit.

In a particular exemplary embodiment, the disclosed radiation blocking capacitive structure may be provided above active circuitry that underlies (and that optionally may surround) capacitive sensor circuitry that is aligned with (e.g., positioned underneath) a package opening that allows ingress of ambient air or other gas into the package. In one possible example, the disclosed systems and methods may be implemented to facilitate placement of radiation-sensitive analog circuitry or other radiation-sensitive circuitry underneath and/or around a capacitive sensor circuit, which will be exposed through one or more package openings to the ambient conditions (e.g., radiation, humidity etc.) for purposes of sensing one or more ambient conditions. Advantageously, the disclosed radiation blocking capacitive structures may be implemented using multiple metal layers where maximum metal width rules prevent a single integrated circuit layer from being dimensioned or otherwise configured to fully block penetration of radiation, such as light, to underlying circuitry.

In one respect, disclosed herein is a multi-layer semiconductor device, including: a first device layer including one or more non-continuous first radiation-opaque layer structures defining radiation transmissive areas in the first device layer; and a second device layer underlying the first device layer, the second device layer including one or more non-continuous second radiation-opaque layer structures defining radiation transmissive areas in the second device layer. The first non-continuous opaque structures of the first device layer may be cooperatively spaced in overlapping relationship with the second non-continuous opaque structures of the second device layer to form a continuous barrier that completely blocks all radiation that impinges on the first device layer from above the semiconductor device from penetrating through the combination of the first and second device layers of the multi-layer structure.

In another respect, disclosed herein is a capacitive gas sensor, including: a gas sensitive material, the gas sensor configured to allow the exposure of the gas sensitive material to a gas; first non-continuous radiation-opaque structures including spaced metal capacitor electrodes of a capacitive sensor cell provided in a first device layer, the capacitive sensor cell being electrically coupled to at least a portion of the gas sensitive material; second non-continuous radiation-opaque structures including one or more metal non-continuous ground planes in a second device layer underlying the capacitor electrodes; and lower level circuitry underlying the capacitive electrodes and ground planes of the first and second device layers. The gas sensor may be configured to utilize a detected capacitance between the electrodes of the capacitive sensor cell to obtain a gas sensor measurement; and the capacitor electrodes of the first device layer may be cooperatively spaced in overlapping relationship with the non-continuous ground planes of the second device layer to block impinging light from further penetration into the lower level circuitry.

In another respect, disclosed herein is a method of forming a multi-layer semiconductor device, the method including: providing a first device layer including one or more non-continuous first radiation-opaque layer structures defining radiation transmissive areas in the first device layer; providing a second device layer underlying the first device layer, the second device layer including one or more non-continuous second radiation-opaque layer structures defining radiation transmissive areas in the second device layer; and configuring the first non-continuous opaque structures of the first device layer to be cooperatively spaced in overlapping relationship with the second non-continuous opaque structures of the second device layer to form a continuous barrier that completely blocks all radiation that impinges on the first device layer from above the semiconductor device from penetrating through the combination of the first and second device layers of the multi-layer structure.

In another respect, disclosed herein is a method of forming a capacitive gas sensor, including: providing a gas sensitive material, the gas sensor provided to allow the exposure of the gas sensitive material to a gas; providing first non-continuous radiation-opaque structures including spaced metal capacitor electrodes in a first device layer of a capacitive sensor cell, the capacitive sensor cell being electrically coupled to at least a portion of the gas sensitive material; providing second non-continuous radiation-opaque structures including one or more metal non-continuous metal ground planes in a second device layer underlying the capacitor electrodes; providing lower level circuitry underlying the capacitive electrodes and ground planes of the first and second device layers; configuring the gas sensor to utilize a detected capacitance between the electrodes of the capacitive sensor cell to obtain a gas sensor measurement; and configuring the capacitor electrodes of the first device layer to be cooperatively spaced in overlapping relationship with the non-continuous ground planes of the second device layer to block impinging light from further penetration into the lower level circuitry.

DESCRIPTION OF THE DRAWINGS

FIG. 10 illustrates capacitor plates for a capacitive sensor structure according to one exemplary embodiment disclosed herein.

FIG. 11 a radiation-blocking shield according to one exemplary embodiment disclosed herein.

DETAILED DESCRIPTION OF THE INVENTION

Figure 1:
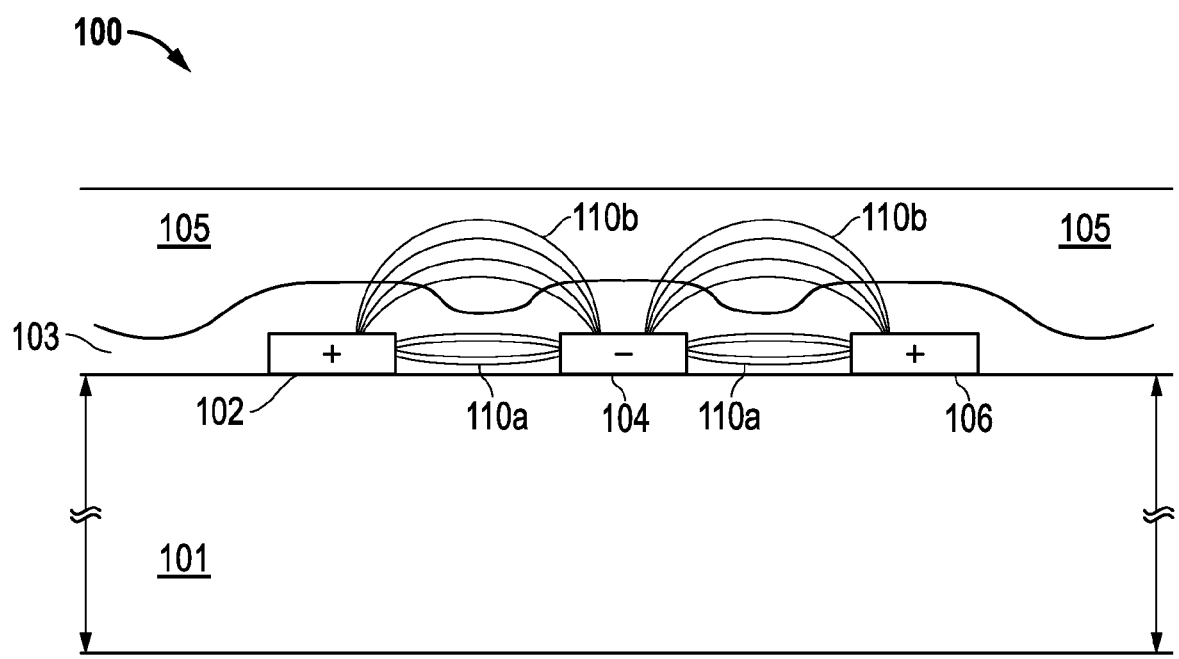
FIG. 1 is an exemplary illustration of a prior art capacitive sensor.

In one exemplary, non-limiting embodiment, the gas and/or humidity sensor system may include two differing capacitive sensor unit cell structures. A first unit cell structure is constructed such that its capacitance measurement is dependent upon capacitance effects that substantially do not extend to the upper reaches of the sensor's gas/humidity sensitive layer and a second unit cell structure is constructed such that its capacitance measurement is dependent upon electric field effects that extend substantially beyond the distance of electric fields of the first unit cell. The capacitance associated with the electric fields in the upper regions of the gas/humidity sensitive layer may then be obtained to a first order by subtracting the capacitance of the first unit cell from the capacitance of the second unit cell. By subtracting the capacitance, a capacitance associated with the capacitance of the electric fields of the layer (or portion of layer) of interest may be approximated while minimizing the effects of other layers, parasitic capacitances, substrate interfaces, the substrate and other stray capacitances. In one embodiment, the electric fields of the first unit cell structure may be confined predominately to layers that do not include the gas/humidity sensitive layer. By subtracting the capacitance, a capacitance associated with the capacitance of the electric fields of the layer of interest (the layer sensitive to a gas or humidity) may be approximated while minimizing the effects of other layers and capacitances. In other embodiments, the number of layers may be minimized such that the electric fields of the second unit cell extend into the gas/humidity sensitive layer but the extent into the gas/humidity layer is to a lesser degree than that the of the first unit cell structure. In such embodiments the subtraction process allows for an isolation of the capacitance effects in the portion of the gas/humidity sensitive layer that is of most interest. As used herein, the term "subtracting" is utilized to convey the concept that the difference between two values is obtained, such as obtaining the difference between the capacitances of two unit cells.

In one exemplary, non-limiting embodiment, a gas and/or sensor is provided in which a capacitive sensor configuration is utilized. The sensor may be comprised of one or more first unit cells and one or more second unit cells. The first unit cell may be constructed to be different from the second unit cell. Moreover, the configuration of the unit cells is such that one unit cell may include capacitance effects of at least a first portion of the gas and/or humidity sensitive layer and other surrounding capacitance effects while the other unit cell includes effects of (1) either none of the gas and/or humidity sensitive layer or smaller portion than the first portion of the gas and/or humidity sensitive layer and (2) the other surrounding capacitance effects. By utilizing measurements from both unit cells, the capacitance effects of the gas and/or humidity sensitive layer (or the most relevant portion of the gas and/or humidity sensitive layer) may be substantially isolated from the effects of the other surrounding capacitance effects. In one exemplary, non-limiting embodiment the utilization of measurements of both unit cells may include a capacitance subtraction process. In one exemplary, non-limiting embodiment the unit cells differ in their periodicity.

In one exemplary embodiment of the techniques described herein, the gas and/or sensor system may include two differing capacitive sensor unit cell structures. One unit cell structure is constructed such that its capacitance measurement is dependent upon capacitance effects that substantially do not include the sensor's gas/humidity sensitive layer and a second unit cell structure is constructed such that its capacitance measurement includes effects of the gas/humidity sensitive layer. The capacitance associated with the electric fields in the gas/humidity sensitive layer may then be obtained to a first order by subtracting the capacitance of the first unit cell from the capacitance of the second unit cell. By subtracting the capacitance, a capacitance associated with the capacitance of the electric fields in the layer of interest (the layer sensitive to a gas or humidity) may be approximated while minimizing the effects of other layers and capacitances. In one exemplary, non-limiting example the gas and/or humidity sensitive layer may be a sensing layer.

In one exemplary, non-limiting embodiment, a gas and/or sensor is provided in which a capacitive sensor configuration is utilized. The sensor may be comprised of one or more first unit cells and one or more second unit cells. The first unit cell may be constructed to be different from the second unit cell. Moreover, the configuration of the unit cells is such that one unit cell may include capacitance effects of a gas and/or humidity sensitive layer and other surrounding capacitance effects while the other unit cell includes the other surrounding capacitance effects but substantially does not include the capacitance effects of the gas and/or humidity sensitive layer. By utilizing measurements from both unit cells, the capacitance effects of the gas and/or humidity sensitive layer may be substantially isolated from the effects of the other surrounding capacitance effects. In one exemplary, non-limiting embodiment the utilization of measurements of both unit cells may include a capacitance subtraction process. In one exemplary, non-limiting embodiment the unit cells differ in their periodicity.

Figure 2A:
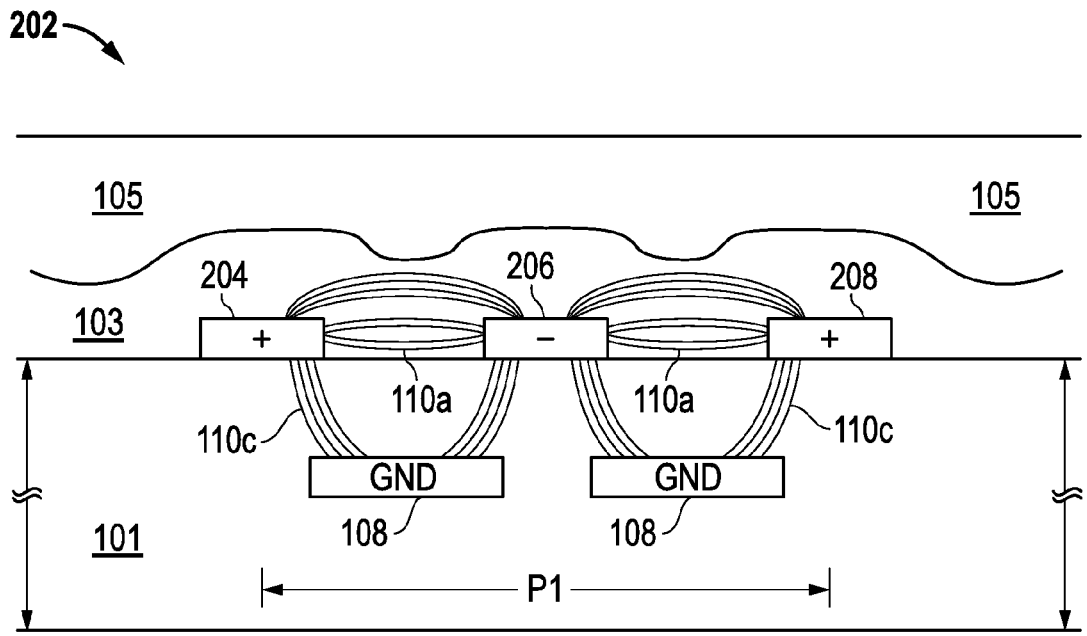
FIG. 2A is an exemplary cross-section illustration of a unit cell structure having a first periodicity.

For example, as shown in FIG. 2a, a first unit cell 202 of a capacitive structure is provided. Similar to FIG. 1, a substrate 101, passivation layer 103 and sensing layer 105 may be provided. Ground planes 108 may also be optionally provided. At least a portion of the upper surface of the sensing layer 105 may be an air/dielectric layer interface and layer 105 may be considered an ambient condition sensitive layer. Sensor electrodes 204, 206, and 208 are also provided. The electrodes 204, 206 and 208 may be sized such that that the electric fields lines predominately reside in areas not within the sensing layer 105 as shown by electric field lines 110c and 110a. It is known that for structures such as shown in FIGS. 1 and 2A that approximately 95% of the electric fields associated which such structures are contained in a region having a height of P divided by two, where P is the periodicity of the unit cell as shown in FIG. 2. More particularly, if the gap between electrodes is Wgap and the width of one of the electrodes is Wwidth, then P=2(Wgap+Wwidth). Thus, the sizing of the periodicity P1 of the cell electrodes and the overlying passivation layer of FIG. 2A may be selected such that the electric fields of the cell structure are limited to regions outside of the sensing layer 105 (i.e. P1/2 is sufficient to keep the electric fields predominately out of the sensing layer). It is noted that for ease of illustration, the figures shown herein are not drawn to scale.

Figure 2B:
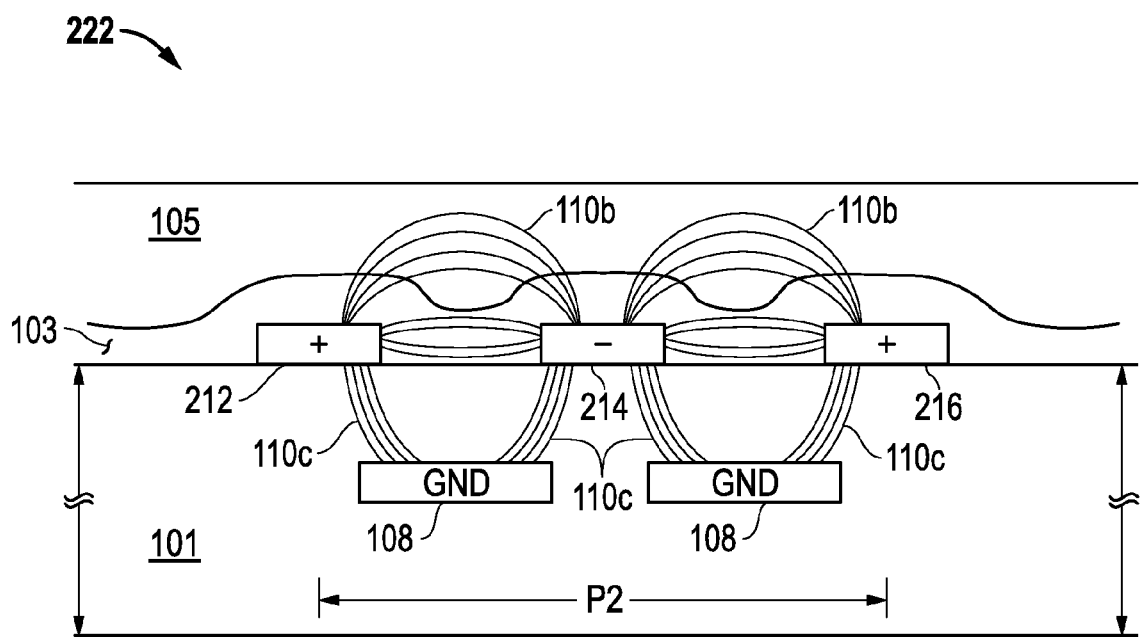
FIG. 2B is an exemplary cross-section illustration of a unit cell structure having a second periodicity that is different from the periodicity of the unit cell of FIG. 2A.

Similarly, as shown in FIG. 2B, a second unit cell 222, different from the first unit cell, is provided. The second unit cell 222 may have a second periodicity P2 that is selected large enough such that P2/2 is sufficiently large such that the capacitor structure electric fields will substantially extend into the sensing layer. Thus, as shown in FIG. 2B, sensor electrodes 212, 214 and 216 are configured in a manner such that significant electric fields 110b extend into the sensing layer 103. The unit cell 202 of FIG. 2A and unit cell 222 of FIG. 2B may both be formed on a common sensor substrate and used together as described below in more detail to provide an improved gas or relative humidity sensor measurement as compared to the prior art techniques. In one embodiment, the period (P2) of the second unit cell 222 may be at least 30% larger than the period (P1) of the first unit cell (note for illustration purposes the unit cells of FIGS. 2A and 2B are not meant to be drawn to scale). In another embodiment, the period of the second unit cell may be at least 50% larger than the period of the first unit cell.

The techniques provided herein allow for the isolation of the effects caused by the electric fields 110b in the sensor dielectric so as to improve the gas or relative humidity measurement accuracy. More particularly, measurements may be obtained with two differing unit cells, such as for example, unit cell 202 and unit cell 222 of FIGS. 2A and 2B. In operation, capacitive measurements obtained from unit cell 202 may be subtracted from capacitive measurements obtained from unit cell 222 to provide a value that is substantially associated with the capacitance of the electric field lines in the sensing layer. For example, if capacitance C1 is the capacitance associated with the unit cell 202 having the smaller periodicity P1 and capacitance C2 is the capacitance associated with the unit cell 222 having the larger periodicity P2, then when C1 is subtracted from C2 the residual (or difference) capacitance is the capacitance primarily associated with the electric field lines in the sensor dielectric. This capacitance associated with the electric field lines in the sensor dielectric (Cd) is the value that primarily reflects the ingress of gas and moisture levels and thus provides an improved value to utilize to correlate to the gas or humidity in the ambient conditions. Thus, a capacitance associated with the electric field lines in the dielectric may be estimated to be Cd=C2−C1. In this manner if the two unit cell capacitors are scaled correctly, to a first order the capacitance associated with the electric field lines in the passivation dielectric, ground planes and other parasitic capacitances may cancel out. Consequently, only changes of capacitance in the region of interest (the gas/humidity absorbing layer, the sensing layer) will produce a net change in the measured capacitance.

Figure 2C:
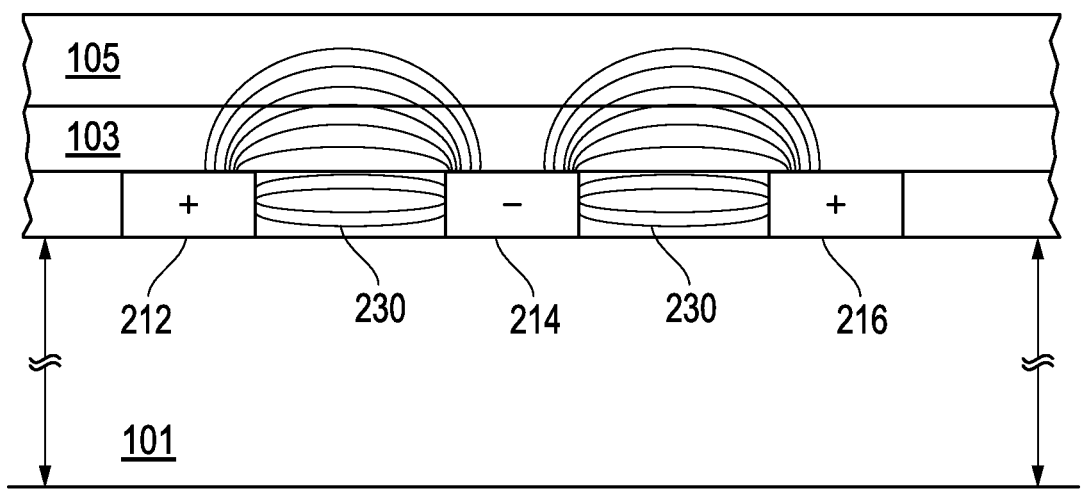
FIG. 2C is an exemplary cross-section illustrating an alternative unit cell configuration.

It will be recognized that the structures and various layers shown in FIGS. 2A and 2B are merely exemplary. For example, numerous integrated circuit processing layers may be included under the sensor electrodes as part of the substrate 101 as known in the semiconductor manufacturing process art (wells, doped layers, isolation layers, transistor gates, interconnects, conductors, vias, etc.). Further, the layers adjacent and above the sensor electrodes may also be varied. For example, as shown in FIG. 2C, the sensor electrodes 212, 214 and 216 may have an adjacent oxide or other dielectric 230. Passivation layer 103 may then be above the dielectric 230 and sensor gas and/humidity sensitive layer 105 may be formed above the passivation layer. Thus, electric fields in the oxide layer 230, passivation layer 103 and sensor gas and/or humidity sensitive 105 may have effects to be considered.

Figure 3A:
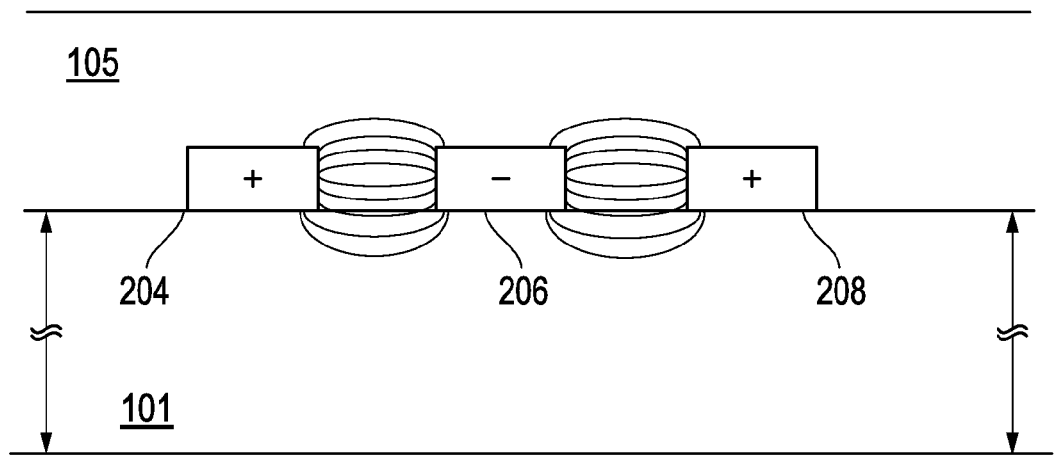
FIGS. 3A-3B are exemplary cross sections of unit cells of differing periodicity as used in an embodiment without a passivation layer under the sensing layer.
Figure 3B:
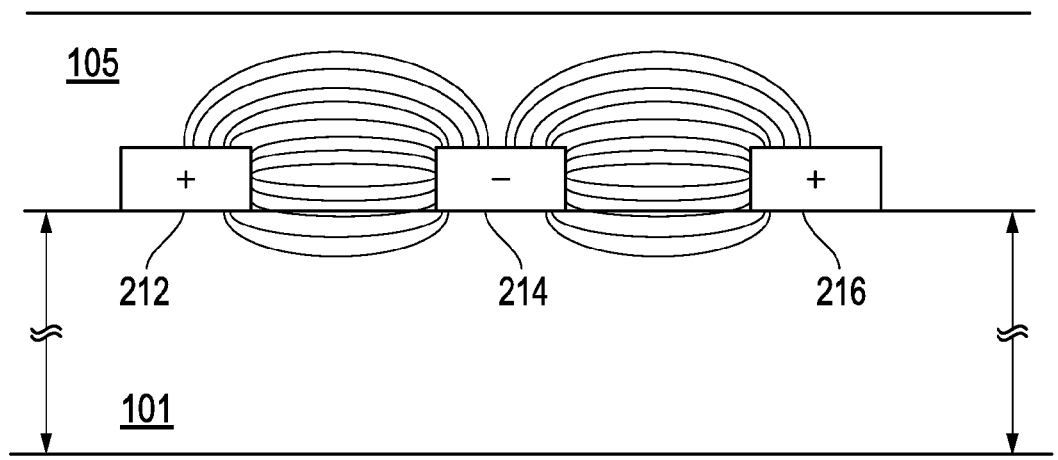

FIGS. 3A and 3B illustrate yet another embodiment of the differing cell techniques described herein. The embodiment of FIGS. 3A-B is similar to that of the embodiment of FIGS. 2A-B except the embodiment of FIGS. 3A-B does not utilize a passivation layer 103. Thus, the sensing layer 105 may be formed around the electrodes without the use of the intervening passivation layer 103. In this embodiment, a portion of electrodes 204 and 208 (note not all of the electrode 204 and 208 are in the unit cell) and electrode 206 form one unit cell 302 and a portion of electrodes 212 and 216 and electrode 216 form another unit cell 322. As shown in FIG. 3A, a unit cell having a smaller period is formed with electrodes 204, 206 and 208. In this cell, the electric fields are predominately contained close to the electrodes deep within the sensing layer. The unit cell of FIG. 3B, however, has a larger period than the unit cell of FIG. 3A, thus providing for an increase electrical field in the upper reaches of the sensing layer 105. In this manner, the effects of the lower portions of the sensing layer 105, fields passing through the substrate 101, any ground planes in the substrate, other substrate interface effects, effects at the interface of the electrodes and other parasitic capacitance effects may be detected with the unit cell of FIG. 3A. The capacitance of the unit cell of FIG. 3A may then subtracted from the detected capacitance of the unit cell of FIG. 3B. The resulting capacitance from such subtraction process will be predominately the capacitance associated with the upper portions of the sensing layer. In this manner, the advantageous of the techniques described above may still be obtained even if layers such as layers 105 and 103 are not present. Thus, the concepts described herein in a broad sense allow for the creation of at least two sets of electric fields, a first set located more close to the electrodes and a second set which extends to a greater distance from the electric field. The capacitance effects detected from the first set of electric fields may be removed from the capacitance effects from the second set. The result of the subtraction process leaves a capacitance value that is dominated by the capacitance of the portions of the sensing layer that are further from the electrodes. This technique provides for a more reliable sensor measurement for determining the particular gas or relative humidity level being detected and a faster sensor.

Though not shown in FIGS. 2C, 3A and 3B, it will be recognized that ground planes may also be present. In one embodiment, the ground planes may be configured to block light from penetrating from the top surface region that is exposed to ambient conditions to circuitry (not shown) that may be formed in the substrate. More particularly, in the sensor unit cell region of the sensor the upper surface of layer 105 may also be exposed to ambient light. Penetration of the light into lower layers below the sensor unit cell capacitor structures may impact circuit operations and performance. In order to prevent such penetration, the ground planes capacitor electrodes may be arranged in a manner that would block impinging light. For some circuits, however, it is not desirable to maintain a continuous ground plane. It address these concerns, for example as shown FIG. 2A, the ground planes 108 may be formed in manner such that the planes are not continuous in regions that associate with the electrodes 204, 206 and 208. Thus, as shown in FIGS. 2A and 2B, the combination of the electrodes and the ground planes would block the ambient light from further penetration into lower level circuitry because the overlap of the ground planes and the electrodes creates in effect a continuous barrier to light penetration. Further description of exemplary embodiments in which multiple layers may be configured to block light or other radiation from penetrating from the top surface region that is exposed to ambient conditions to underlying circuitry is described below in relation to FIGS. 5-18.

The techniques described herein to isolate the capacitance effects of the sensor gas and/or humidity sensitive layer may be utilized with all such variations of the overall device layers and structures. Further, any of the layers described herein may be shown for ease of illustration as a single layer, however, it will be recognized that such layers may be formed of a composite of many layers of the same or different material.

A variety of techniques may be utilized to subtract the capacitance effects of the differing unit cells and the concepts disclosed herein need not be limited to a particular technique. For example, the two capacitors can be measured individually and the measurements converted to digital values. The digital values may then be subtracted. Such a technique removes the need for weighting the capacitors. Alternatively when weighted correctly, the capacitors may subtracted utilizing amplifier summing node techniques to provide a value that is representative of subtracted capacitance. The techniques described herein may be utilized by simultaneously measuring the capacitance of each unit cell or alternatively one or the other unit cell may be measured serially before the other.

Figure 4:
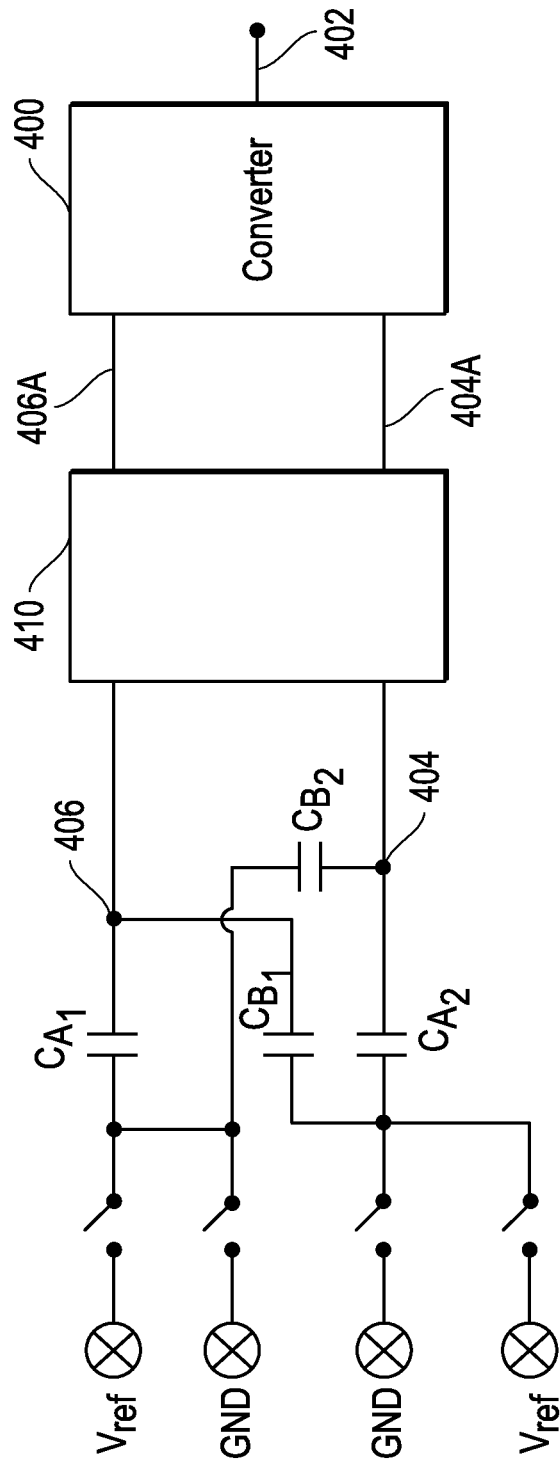
FIG. 4 is an exemplary circuit for subtracting the capacitance effects of differing unit cells.

One exemplary technique for subtracting the various capacitances is the amplifier summing node technique shown in FIG. 4. As shown in FIG. 4 an differential summing technique is provided for unit cells having differing capacitances. Capacitors CA1 and CA2 are the capacitances formed from unit cells having a larger period. Capacitors CB1 and CB2 are the capacitances formed from unit cells having a smaller period. Reference voltages Vref and GND are applied as shown to the unit cells. Nodes 406 and 404 are coupled to a switching circuit 410. In operation, in one phase (when CA1 and CB2 are coupled to Vref and CA2 and CB1 are coupled to GND), switching circuitry 410 connects node 406 to node 406A and connects node 404 to node 404A. In another phase (when CA1 and CB2 are coupled to GND and CA2 and CB1 are coupled to Vref), switching circuitry 410 connects node 406 to node 406A and connects node 404 to node 406A. Nodes 406A and 404A are coupled to a converter 400 which converts the detected charge to a digital value at node 402. In one embodiment, converter 400 may be a switched capacitor sigma-delta converter. In this manner, the digital value at node 402 may be representative of a subtraction of capacitance CB from capacitance CA. The example described with reference to FIG. 4 is merely illustrative and it will be recognized that many other techniques may be utilized to obtain a representation of the subtraction of the one unit cell capacitance from another unit cell capacitance, and the disclosure herein is not meant to be limited to any such particular technique.

As described above, the techniques provided herein help remove the effects of the capacitance associated with electric fields that are either outside of the sensor dielectric or outside of the most relevant portions of the sensor dielectric. Removing such effects is particular advantage as these other capacitances may have non-ideality variations related to temperature changes, long term aging, chemical and physical contamination, etc. Thus removing the capacitances associated with the electric fields outside of the most relevant portions of the sensor dielectric helps minimize the impact of variations in such other electric fields caused by temperature, aging, contamination, etc. Furthermore, as many of these degradation effects may change over time, the techniques provided herein provide an improved sensor in that the long term drift of the sensor readings are reduced. The techniques provided herein may also reduce the impact of any degradation in the air/sensing layer interface. Because the region of interest in the sensor structure is reduced to the electric fields in the sensing layer or the portions of the sensing layer of interest, the sensor response time may be reduced.

As described above, capacitors having differing structures are utilized to help isolate the capacitance effects in the sensor material of interest from other capacitance effects caused by surrounding structures of the sensor. One non-limiting illustrative technique of isolating the impact of the material of interest is the differing periodicity of the unit cells. However, the techniques provided herein may be utilized by many other approaches to isolate the capacitance effects in the sensor dielectric material. For example, the periodicity of each cell may remain constant; however, the ratio of Wgap/Wwidth may be changed in each cell so as to change the electric field patterns. Similarly, the thickness of the passivation layer may be different between each unit cell so as to change the electric field patterns. Further, though shown with regard to the presence of substrate ground planes, it will be recognized that such ground planes need not be utilized. Other, techniques for providing differing cells may include changing the layers above or below the sensor electrodes between the two differing cells. Thus, for example, the differing cells may differ in the number of layers above or below a particular cell. In such cases, the cells may be configured to target/isolate the effects of individual sensing layers or particular portions of the sensing layers. The unit cells may also differ in that one cell may have the sensor dielectric directly deposited on the sensor electrodes without the use of a passivation layer and the other cell does not.

Though exemplary embodiments are described herein with regard to unit cells constructed to be different, it will be recognized that the unit cells may be originally constructed in a uniform fashion and then subsequently electrically programmed to be differing. Thus, a programmable unit cell may also be utilized. For example, the unit cells may be comprised of a series of similar capacitive interdigitated "finger" structures. Then various fingers of the structures may be electrically removed or added (switched in or out) so that differing unit cells may be programmable created. Thus, for example, a series of evenly spaced fingers forming electrodes may be utilized to create two different unit cells by one unit cell using each electrode finger while another unit cell has every other electrode finger electrically isolated (switched out of the measurement) and not utilized in the measurement. In this fashion even though all the electrodes were originally formed to have a common periodicity, the sensor may be electrically programmed to provide a first set of electrodes having one periodicity to be used for measurements and a second set of electrodes having a differing periodicity. In yet another programmable embodiment, the electrode fingers for each unit cell may include a set of common electrodes utilized in both unit cells. Thus for example, a serial measurement technique may be utilized in which a first measurement is obtained utilized a first set of electrode fingers which are selected via an electrically programmable technique. Then a second measurement may be obtained utilizing a second set of electrode fingers which were selected via an electrically programmable technique such that the first set of electrode fingers is different than the second set of electrode fingers, though each set may have electrode fingers that are common to the other set. In such a serial approach, having different electrode fingers programmable selected for each measurement provides differing unit cell structures for each measurement that may be selected to isolate the capacitance effects of the sensor's ambient condition sensitive layer. The use of programmable electrode fingers that may optionally switched in and out of the measurement structure may also be utilized to calibrate the sensor. Thus, no matter whether the unit cells are originally constructed to be the same or constructed originally different, programmable switchable cell structures may be utilized to fine-tune or calibrate the overall sensor. It will be recognized that electrically programmable cell structures provides a near endless arrangement of cell structures and that the descriptions provided herein are merely example programmable techniques for creating differing cell structures and that the disclosed herein is not limited to only the techniques described for illustrative purposes.

Thus, the techniques of creating differing electrical field patterns, obtaining measurements from the differing electric field patterns and utilize that data so as to isolate various differing capacitance effects may be achieved in wide ranging variety of manners. In this manner, the benefits of the concepts described herein are not limited to the particular structures shown herein and it will be recognized that the overall concepts disclosed herein are not so limited.

In one embodiment, the portion of the sensor dielectric capacitance that remains after the subtraction process may include electric fields that substantially extend to the ambient air/sensor dielectric interface, such as disclosed in the application concurrently filed on the same date as the present application, U.S. patent application Ser. No. 13/557,739, entitled "SENSOR FOR MEASURING HIGH HUMIDITY CONDITIONS AND/OR CONDENSATION"; the disclosure of which is expressly incorporated by reference herein in its entirety. In such techniques, the capacitance of moisture on the surface interface may be measured by configuring one of the unit cells such that a substantial portion of the electric fields extends to the surface interface. The capacitance of the other unit cell may then be subtracted to provide a more reliable humidity sensor reading that may extend to the detection of condensation. Extrapolating the disclosed techniques even further, in one embodiment, the unit cells could be sized such that the dominate capacitance that remains is the capacitance at or even above the ambient air/sensor layer interface.

Also though shown illustratively herein as straight subtraction, it will be recognized that subtraction incorporates a weighted subtraction such as: $Cd=aC2-bC1$, where a and be may be weighting functions. Alternatively, the concepts described herein are not merely limited to subtraction techniques. Thus, when given the configuration of two or more differing unit cells, more complex mathematical techniques may also be utilized to isolate the impact of the capacitance effects of the gas and/or humidity sensitive layer. Further, it will be recognized that the capacitors described herein are shown with regard to one unit cell, each differing capacitor structure may be formed from only one unit cell or from many of such unit cells combined. Finally, though the techniques are described with regard to two differing unit cells, the techniques described herein may be extrapolated to the use of three or more unit cells each differing from the others wherein the measurements of the cells is performed in a manner so that the effects of gas or relative humidity changes on the sensor dielectric may be isolated.

In the exemplary differing unit cells of FIGS. 2A and 2B, the electric fields of FIG. 2A are described as predominately not extending into the sensing layer 105. Further, in FIG. 3A the electric fields are not shown extending to the upper portions of the sensing layer 105. It will be recognized that theoretically the electric fields extend in increasing infinitesimally small amounts over great distances. However, the techniques described herein may be advantageous if such electric fields are predominately reduced in the desired portion of the sensor dielectric by at least one-third, and in a preferred embodiment by 50% and in an even more preferred embodiment by two-thirds. Thus in one embodiment, a substantial reduction of the electric fields, a reduction of approximately at least 50%, utilizing the techniques such as described above would be advantageous.

Thus as described herein differing unit cells may be constructed so that the electric field behavior of the unit cells is different. In particular, one unit cell may be constructed such that the portion of the electric filed in the region of the sensing layer (as compared with the total electric field across all regions) is higher than that of the other unit cell. Thus, a first unit cell may create proportionally less of an electric field in the areas of interest (as compared to the areas of non-interest) and a second unit cell may create proportionally more of an electric field in the areas of interest (as compared to the areas of non-interest). Knowing the existence of these differing proportional field strengths may then be utilized to combine measurements of both unit cells in a manner in which the behaviors of the regions of interest are emphasized.

The concepts described herein are not limited to particular materials or particular unit cell sizing. In one exemplary, non-limiting embodiment a sensor in conformance with the embodiment of FIGS. 3A and 3B may be formed. The sensor electrodes may be formed of aluminum, copper, gold, titanium, refractory metals, or any other conductor material as known for potential use in integrated circuit manufacturing, and the sensor ambient sensitive material may be formed of a polyimide, in one example BDMA (benzyldimethylamine) and other polyimides types, such as PBOs, BCB and the like. It will be recognized that many other polyimides or other industry standard ambient sensitive materials may be utilized.

Further, exemplary non-limiting dimensions may include unit cell periodicity of unit cell 302 of about 1 microns to 5 microns (with an exemplary embodiment of Wgap 2 microns and Wwidth 2 microns) and unit cell periodicity of unit cell 322 of about 8 microns to 12 microns (with an exemplary embodiment of Wgap 4 and Wwidth 4). As mentioned above the unit cells may be single unit cells or a combination of unit cells. In one exemplary embodiment, the sensor dielectric thickness may be approximately in the range of 1 micron to 10 microns and the conductive electrodes may have a thickness of 0.5 microns to 2 microns.

In one exemplary embodiment, the sensor structure disclosed herein may be a relative humidity sensor formed on the upper surface of an integrated circuit. The integrated circuit may include circuitry, processors, memory and the like providing gas concentration and/or relative humidity readings based upon the detected changes in the gas and/or humidity sensitive layer. In one exemplary embodiment the upper surface area of the integrated circuit may be approximately 4 $mm^2$. A cavity may be formed in the package of the integrated circuit to expose roughly a 0.5 $mm^2$ area of the sensor dielectric. Four capacitors may be formed, two unit cells 302 and two unit cells 322 and configured in a differential mode such as shown in FIG. 4. The larger period capacitors may occupy an area of approximately 0.15 $mm^2$ per capacitor and the smaller period capacitors may occupy an area of approximately 0.06 $mm^2$ per capacitor.

As previously described and illustrated in relation to FIGS. 2A and 2B, ground planes 108 may be arranged beneath first unit cell capacitor electrodes 204, 206 and 208 (and second unit cell electrodes 212, 214 and 216 of FIG. 2B) in a manner that blocks radiation such as impinging ambient light from penetrating from the top surface region that is exposed to ambient conditions to circuitry that may be formed in the substrate 101. In particular, the ground planes 108 may be formed in manner such that the planes are not continuous in regions that associate with the electrodes 204, 206 and 208 such that the combination of the electrodes and the ground planes block ambient light or other radiation from further penetration into lower level circuitry because the overlap of the ground planes and the electrodes creates in effect a continuous barrier to penetration of light or other radiation.

Figure 5:
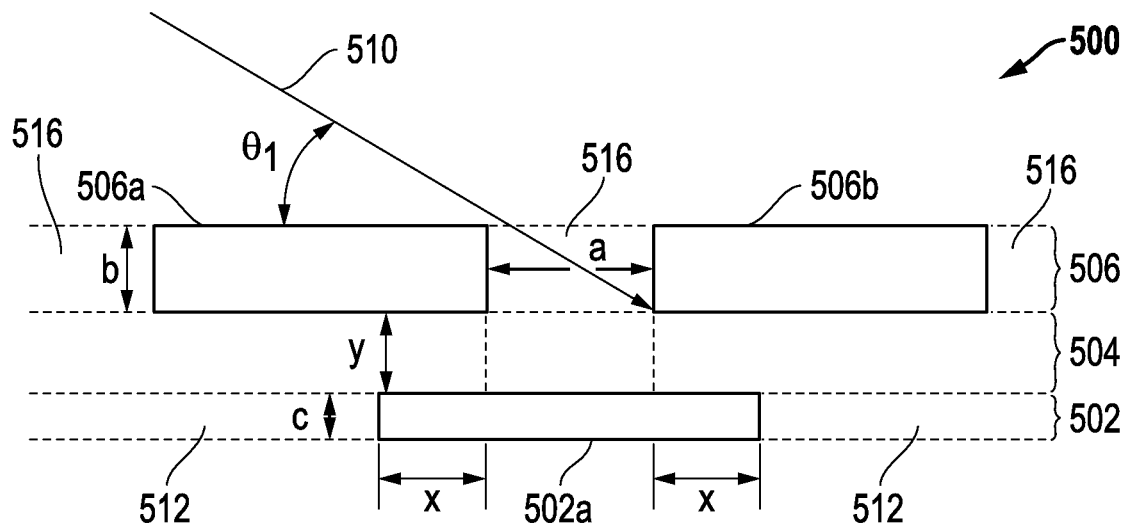
FIG. 5 illustrates a structural relationship stacked integrated circuit processing layers according to one exemplary embodiment disclosed herein.
Figure 6:
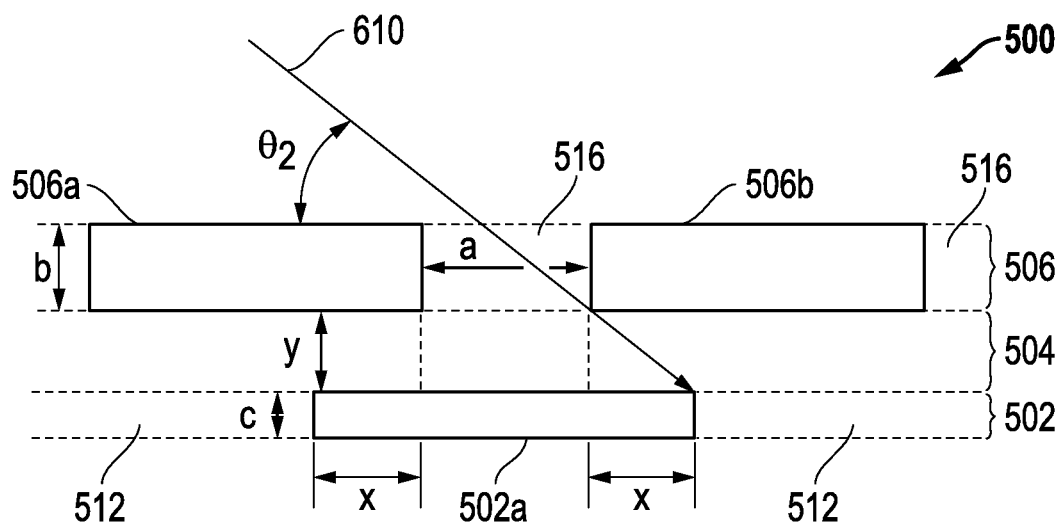
FIG. 6 illustrates a structural relationship stacked integrated circuit processing layers according to one exemplary embodiment disclosed herein.
Figure 7:
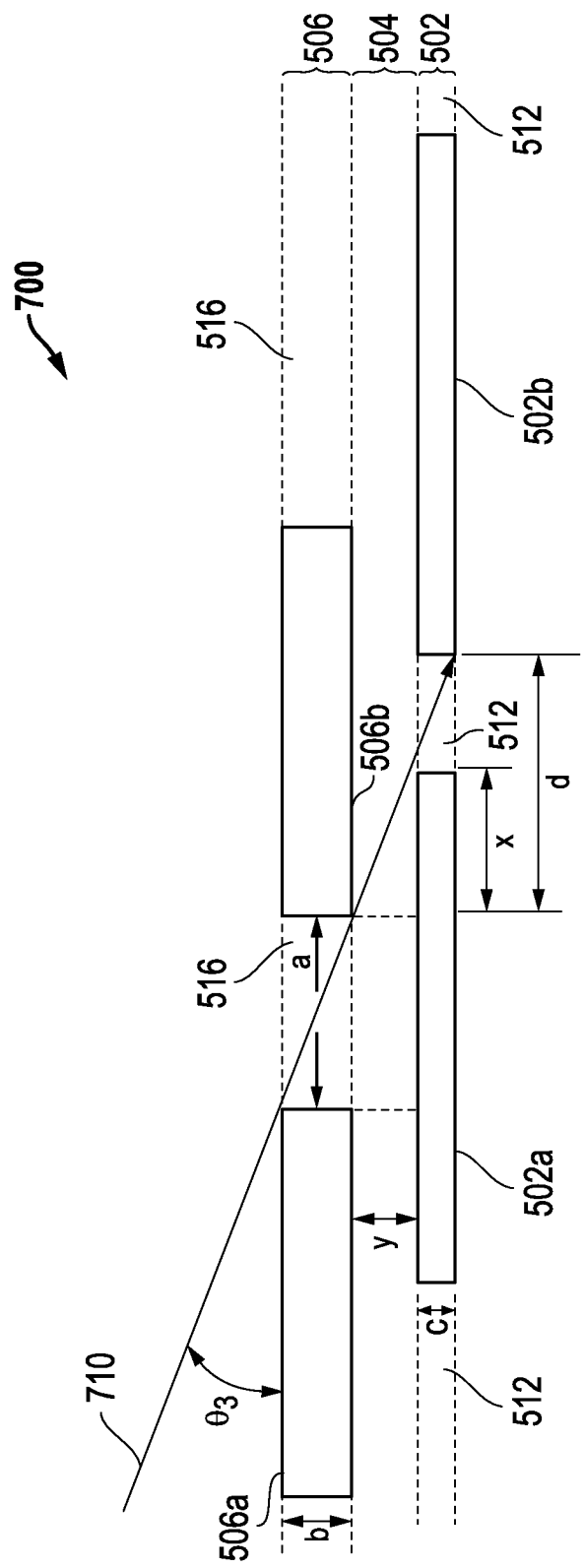
FIG. 7 illustrates a structural relationship stacked integrated circuit processing layers according to one exemplary embodiment disclosed herein.

FIGS. 5-7 illustrate exemplary embodiments of relative positioning and dimensional relationships that may be employed to select particular configurations of stacked layers of non-continuous opaque layer structures to achieve radiation blocking, e.g., such as metal layer structures for a semiconductor device as illustrated in relation to FIGS. 2A and 2B (note for illustration purposes structures of FIGS. 5-7 are not meant to be drawn to any particular scale). In this regard, two stacked opaque (e.g., metal) layer structures may be configured in one embodiment to block radiation received at a low incident angle so that it cannot penetrate beyond the stacked combination of the two opaque layer structures. Further, complete radiation blocking for all received angles of incident radiation may be achieved in another embodiment by utilizing adjacent opaque layer structures (e.g., such as capacitor finger electrodes) to confine incident radiation within a specific region of the stacked structure. It will be understood that a radiation-blocking structure may be configured with non-continuous layer structures that are composed of material/s that are opaque to one or more given types or bands of radiation, i.e., that are opaque to, and non-transmissive of, the given type/s or band/s of radiation to be blocked. Examples of such opaque materials include the metal material of metal 1 to metal 6 layers in a standard CMOS process which are opaque to electromagnetic radiation, e.g., such as visible light radiation, infrared radiation and ultraviolet radiation. It will be understood that the type/s of radiation blocked may vary with the type of particular type of opaque material/s employed.

In one embodiment, such non-continuous opaque layer structures may be configured as stacked non-continuous metal layers that together fully block penetration of radiation while at the same provide sufficient open spaces between and/or within the metal layer segments of a given integrated circuit layer to meet foundry maximum metal spacing rules. Such metal spacing rules require sufficient open (non-metal) area be defined within the metal of an integrated circuit layer to provide stress relief for the metal by ensuring that all metal structure segments having dimensions greater than N×N have an opening defined in each of such segments to provide stress relief and to prevent loss of metal adherence. In this regard, "N" is a dimensional value that is particular for each process, e.g., N=25 microns for a 0.18 micron process such that all 0.18 micron process metal structure segments having dimensions greater than 25 microns×25 microns must have an opening defined in each of such segments to provide stress relief and to prevent loss of metal adherence.

It will be understood that the radiation-blocking embodiments of FIGS. 5-7 are not limited to implementation as capacitive and ground plane metal layer structures such as illustrated in relation to FIGS. 2A and 2B, but may be implemented in any other type of multi-layer semiconductor device configuration having underlying radiation-sensitive circuitry, e.g., such as infrared proximity chips, chips with FLASH memory circuitry, etc. Further, the different multiple opaque layer structures of FIGS. 5-7 may correspond to respective separate layer structures of a common active or passive circuit element, may correspond to layer structures of respective different semiconductor circuit elements, or any one or more of the non-continuous opaque layer structures may correspond to non-circuit element components of a semiconductor device.

FIGS. 5-7 illustrate exemplary embodiments in which two semiconductor device layers 502 and 506 including non-continuous opaque layer structures are stacked on top of each other with an intervening radiation-transmissive layer 504 (e.g., translucent or at least partially transparent to light or other radiation) positioned therebetween. It will be understood that the disclosed systems and methods may also be implemented in other embodiments to configure three or more layers of non-continuous opaque layer structures that are stacked on top of each other with one or more intervening radiation-transmissive layers stacked between each adjacent layer pair of non-continuous opaque layer structures in a manner that at least partially or completely blocks radiation transmission through the multiple layers of the layer structure. Furthermore, it will be understood that a minimal number of opaque layer structures for each of respective semiconductor device layers 502 and 506 are illustrated in FIGS. 5-7 as an example only, and that a greater number of such non-continuous opaque layer structures may be provided for each for layers 502 and 506, e.g., in a repeating pattern across the circuit area of a semiconductor device.

Referring now to FIG. 5, a structural relationship 500 of three stacked integrated circuit processing layers 502, 504 and 506 is shown. In this embodiment, each of layers 502, 504 and 506 lies in a plane that is oriented parallel to the plane of each of the other layers 502, 504 or 506. In one exemplary embodiment, underlying layer 502 may correspond to metal 5, overlying layer 506 may correspond to metal 6, and intervening radiation-transmissive layer 504 may correspond to an radiation-transmissive insulating layer, such as silicon dioxide, of a semiconductor integrated circuit. Although an exemplary embodiment including uppermost metal 5 and metal 6 layers of an integrated circuit structure are illustrated herein, it will be understood that the disclosed radiation blocking structures may be implemented using any combination of two or more stacked layers, e.g., such as N and N-1 layers of an integrated circuit structure having a total of N layers with layer N being the top layer. Also possible is implementation of the disclosed radiation blocking in interior or lower levels, e.g., such as N-2 and N-3 layers where the N and N-1 layers are radiation-transmissive.

In the illustrated embodiment, underlying layer 502a includes a non-continuous opaque layer structure 502a (e.g., metal 5 structure such as ground plane structures of FIGS. 2A and 2B) and overlying layer 506 includes spaced non-continuous opaque layer structures 506a and 506b (e.g., metal 6 structures such as interdigitated capacitor electrode structures of FIGS. 2A and 2B). Intervening radiation transmissive layer 504 may be a translucent or transparent oxide or other dielectric, as may be the areas 512 and 516 of layers 502 and 506 that surround the respective opaque layer structures 502a, 506a and 506b. It will be understood, however, that the positioning and dimensional relationships illustrated in FIGS. 5-7 are applicable to any other type of multi-layer semiconductor device having non-continuous opaque structures provided on at least two different layers or levels, with the non-continuous opaque structures on the different layers or levels being cooperatively spaced or staggered to at least partially overlap with each other in a manner so as to partially or completely block radiation from penetrating through the multi-layer structure.

In the embodiment of FIG. 5, overlying non-continuous adjacent top opaque layer structures (e.g., metal fingers) 506a and 506b have a structure thickness "b" defined by the thickness of layer 506, and are spaced apart from each other by an inter-structure spacing distance "a". Underlying non-continuous opaque layer structure 502a has a structure thickness "c" and is spaced apart from non-continuous opaque layer structures 506a and 506b by an inter-layer distance "y", which in this embodiment also corresponds to thickness of intervening radiation transmissive layer 504. As further shown, each of overlying non-continuous opaque layer structures 506a and 506b overlap underlying non-continuous opaque layer structures 502a by an overlapping distance "x".

In the embodiment of FIG. 5, overhead radiation 510 (e.g., such as ambient light) is shown striking upper layer 506 from above and entering the radiation-transmissive area 516 at an upper peripheral edge of opaque layer structure 506a and at an incident angle $\Theta_1$ relative to the plane of layers 502/504/506. As shown, radiation 510 penetrates radiation-transmissive area 516 until it is stopped at the point where it strikes a lower peripheral corner of adjacent opaque layer structure 506b. Accordingly, any incident radiation striking layer structure 500 at an angle less than or equal to $\Theta_1$ will therefore be blocked by either opaque layer structure 506a or 506b, with $\Theta_1$ being dependent on the particular thickness "b" for a given spacing of adjacent top opaque layer structures 506a and 506b, and vice-versa. Thus, in this embodiment, $\Theta_1$ is the maximum angle to the layer plane at which overhead incident radiation entering area 516 will be blocked by one of adjacent opaque layer structures 506a and 506b for a given structure thickness "b" and inter-structure spacing "a" of these opaque layer structures. In one embodiment, $\Theta_1$ may be expressed by the following relationship:

$$\Theta_1 = \sin^{-1}\left[\frac{b}{\sqrt{a^2 + b^2}}\right]$$

Thus, in one embodiment, where a=3 microns, b=0.99 microns, x=3.1 microns, and y=1 microns, the value of $\Theta_1$=18.26 degrees.

FIG. 6 illustrates the same structural relationship 500 of FIG. 5, but this time with overhead radiation 610 shown striking upper layer 506 from above at an incident angle $\Theta_2$ relative to the plane of layers 506/504/502, and entering the radiation-transmissive area 516 between adjacent top opaque layer structures 506a and 506b. As shown, radiation 510 penetrates radiation-transmissive area 516 and radiation transmissive layer 504 until it is stopped at the point where it strikes a rightmost upper peripheral corner of underlying opaque layer structure 502a. Accordingly, any incident radiation striking layer structure 500 at an angle greater than or equal to $\Theta_2$ will therefore be blocked by underlying opaque layer structure 502a due to the overlap of the stacked opaque layer structures of layers 506 and 502 with $\Theta_2$ being dependent on the particular combination of structure thickness "b", overlap distance "x" and inter-layer distance "y". Thus, in this embodiment $\Theta_2$ is the minimum angle to the layer plane at which overhead incident radiation entering area 516 will be blocked by the underlying opaque layer structure 502a for a given combination of overlap distance "x" of opaque layer structures 506a/506b with underlying opaque layer structure 502a, and inter-layer distance "y" between opaque layer structures 506a/506b and underlying opaque layer structure 502a. In one embodiment, $\Theta_2$ may be expressed by the following relationship:

$$\Theta_2 = \sin^{-1}\left[\frac{y}{\sqrt{x^2 + y^2}}\right]$$

Thus, in one embodiment, where a=3 microns, b=0.99 microns, x=3.1 microns, and y=1 microns, the value of $\Theta_1$=17.88 degrees.

Therefore, in one exemplary embodiment FIGS. 5, and 6, complete blocking of overhead radiation may be achieved using a structural relationship such as shown in FIGS. 5 and 6 by appropriate configuration of "a", "b", "y" and "x" dimensions of the structural relationship 500 such that $\Theta_2 \leq \Theta_1$, or in other words such that the following relationships are true:

$$\sin^{-1}\left[\frac{y}{\sqrt{x^2 + y^2}}\right] \leq \sin^{-1}\left[\frac{b}{\sqrt{a^2 + b^2}}\right]$$

or $$x \geq \frac{y*a}{b}$$

To illustrate one possible application of the above-described relationship 500 for the case of a 0.18 micron integrated circuit process, the value of "b" is fixed to 0.99 microns and value of "y" is fixed to 1 micron, although the other dimensions may be varied to achieve complete radiation blocking. Assuming that the value of "a" is first independently selected to be 3 microns, then the value of "x" must be greater than or equal to 3.03 microns to achieve complete radiation blocking. In one embodiment having such dimensions, value of "x" may accordingly selected to be 3.1 microns to ensure that complete radiation blocking is achieved. It will be understood that fixed values of "b" and "y" may vary for other process scales, and in some embodiments all dimensional values may be varied as needed or desired. Moreover, where "b" and "y" are fixed by the process, then it is alternatively possible to first independently select the value of "x" and then calculate the maximum value of "a" using the above relationship to achieve complete radiation blocking.

FIG. 7 illustrates another possible structural relationship 700 of three stacked integrated circuit processing layers 502, 504 and 506 that may be alternatively implemented to achieve complete radiation blocking, e.g., without the necessity of achieving the $\Theta_2 \leq \Theta_1$ angular relationship described in relation to FIGS. 5 and 6. In this illustrated embodiment, adjacent underlying opaque layer structures 502a and 502b are configured and spaced as shown to achieve a particular underlap distance "d" from a leftmost peripheral edge of overlying opaque layer structure 506b to the leftmost peripheral edge of an underlying opaque layer structure 502b as shown. This time overhead radiation 710 is shown striking upper layer 506 from above at an incident angle $\Theta_3$ relative to the plane of layers 506/504/502, and entering the radiation-transmissive area 516 between adjacent top opaque layer structures 506a and 506b. As shown, this radiation 710 striking at incident angle $\Theta_3$ is not blocked from entering layer 504 by adjacent opaque layer structure 506b. In one embodiment, $\Theta_3$ may be expressed by the following relationship:

$$\Theta_3 = \sin^{-1}\left[\frac{c}{\sqrt{c^2 + (d-x)^2}}\right]$$

As shown in FIG. 7, radiation 710 penetrates radiation-transmissive area 516, radiation transmissive layer 504, and radiation-transmissive area 512 until it is stopped at the point where it strikes a leftmost lower peripheral corner of underlying opaque layer structure 502b. Accordingly, any incident radiation striking layer structure 500 at an angle less than or equal to $\Theta_3$ will therefore be blocked by underlying opaque layer structure 502b due to the underlap of the stacked opaque layer structures of layer 502 and 506 with the value of $\Theta_3$ being dependent on the particular combination of structure thicknesses "b" and "c", underlap distance "d" and inter-layer distance "y". Thus, in this embodiment $\Theta_3$ may be described as the maximum angle to the layer plane at which incident radiation entering area 516 will be blocked by the underlying opaque layer structure 502b for a given combination of thicknesses "b" and "c" of respective overlying and underlying opaque layer structures 506a/506b and 502b, underlap distance "x" of underlying opaque layer structure 502b with overlying structures 506a/506b, and inter-layer distance "y" between overlying opaque layer structures 506a/506b and underlying opaque layer structure 502a.

Therefore, in one exemplary embodiment complete radiation blocking may be achieved using a structural relationship such as shown in FIGS. 6 and 7 by appropriate configuration of "x", "c", "d" and "y" dimensions of the structural relationship 700 such that the following relationship is true: $\Theta_3 \geq \Theta_2$, or in other words such that the following relationships are true:

$$\sin^{-1}\left[\frac{c}{\sqrt{c^2 + (d-x)^2}}\right] \geq \sin^{-1}\left[\frac{y}{\sqrt{x^2 + y^2}}\right]$$

or $$d \leq \frac{x*(c+y)}{y}$$

To illustrate one possible application of the above-described relationships for the case of a 0.18 micron integrated circuit process, the value of "y" is fixed to be 1 micron, and the value of "c" is fixed to be 0.53 microns, although the other dimensions may be varied to achieve complete radiation blocking. Assuming that the value of "x" is first independently selected to be 3 microns, then the value of "d" must be less than or equal to 4.59 microns to achieve complete radiation blocking. In one embodiment having such dimensions, value of "d" may accordingly selected to be 5.1 microns to ensure that complete radiation blocking is achieved. It will be understood that fixed values of "c" and "y" may vary for other process scales, and in some embodiments all dimensional values may be varied as needed or desired. Moreover, where "c" and "y" are fixed by the process, then it is alternatively possible to first independently select the value of "d" and then calculate the maximum value of "x" using the above relationship to achieve complete radiation blocking.

Figure 8:
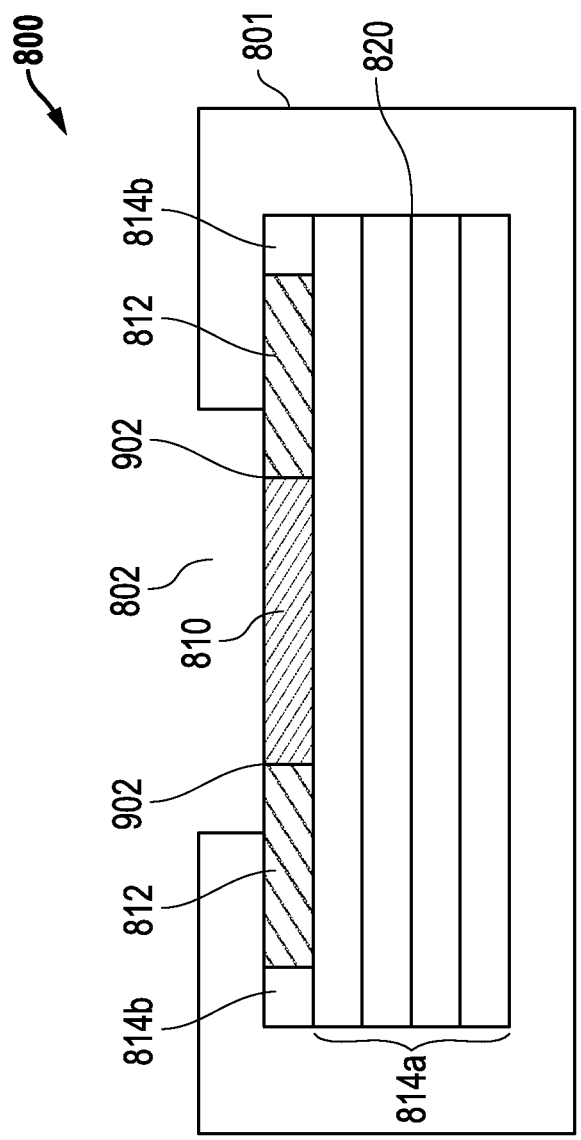
FIG. 8 illustrates a simplified cross-sectional view of a packaged integrated circuit device according to one exemplary embodiment disclosed herein.
Figure 9:
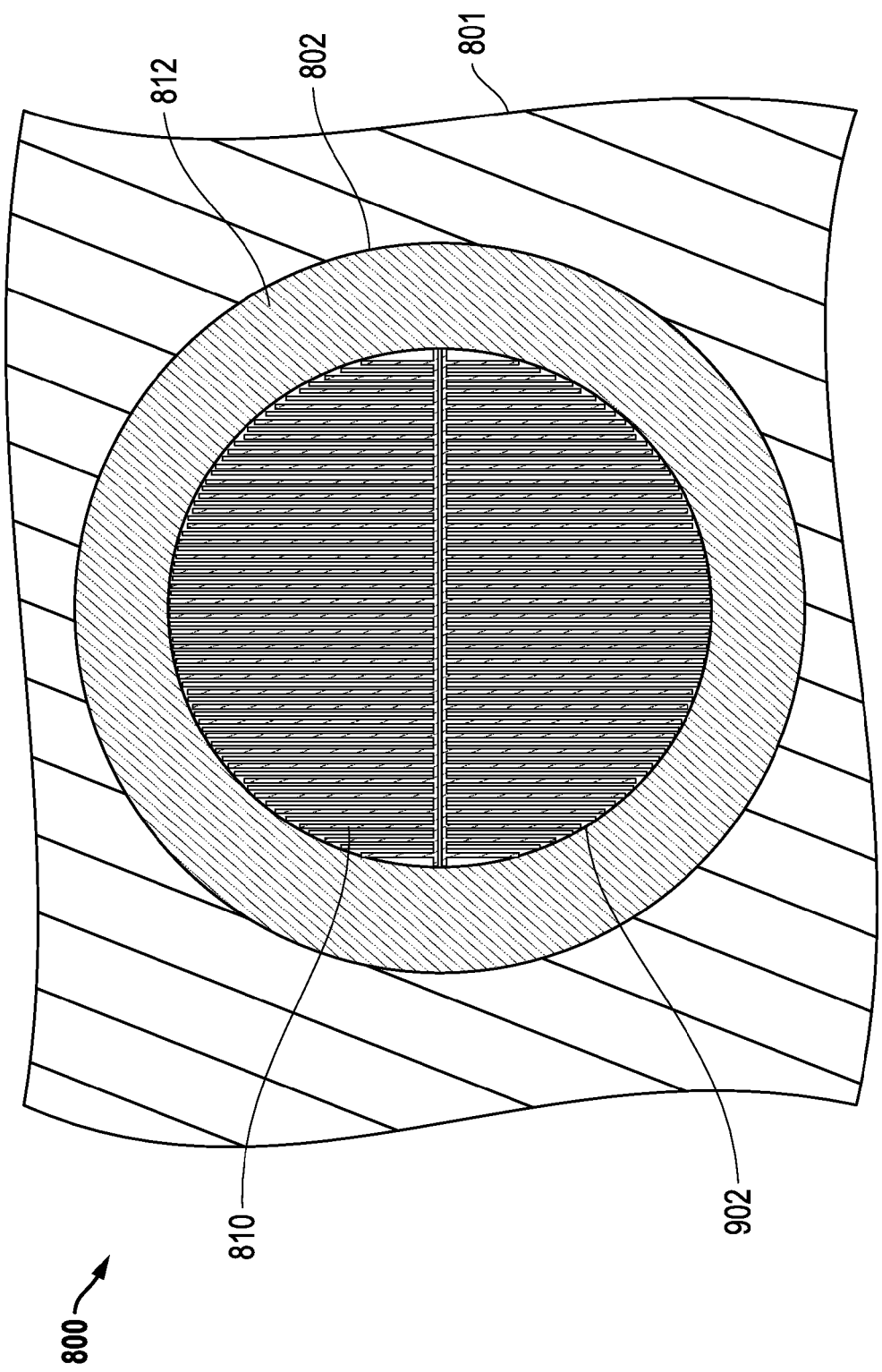
FIG. 9 illustrates a simplified top view of a packaged integrated circuit device according to one exemplary embodiment disclosed herein.

FIG. 8 is a simplified illustration of one exemplary embodiment of a packaged integrated circuit device 800 that includes a sensor system 820 contained within a package 801 (e.g., epoxy encapsulant, ceramic, etc.). In one exemplary embodiment, package 801 may be constructed of a material that is substantially opaque to one or more types of electromagnetic radiation (e.g., such as sunlight, artificial light, ultraviolet radiation, infrared radiation, etc.). In this illustrated embodiment, sensor system 820 includes a capacitive sensor circuitry area 810 that itself includes unit cells of a capacitive structure (e.g., formed in uppermost integrated circuit layers 5 and 6) such as previously described in relation to FIGS. 2-4 herein. As further shown, an area of other radiation-blocking capacitor structures 812 (e.g., also formed in uppermost integrated circuit layers 5 and 6) is present to surround capacitive sensor circuitry area 810. Other capacitor structures 812 may be, for example, bypass capacitors to reduce noise (e.g., coupled between a digital supply and ground, coupled between an analog supply and ground, coupled between an internal regulated supply and ground, etc.), decoupling capacitors, etc. Underlying each of areas 810 and 812 may be radiation sensitive digital and/or analog circuitry layers 814a (e.g. formed in integrated circuit layers 1-4) such as FLASH memory circuitry, any low power analog circuitry, etc. It is noted that for illustration purposes the package, layers and structures of FIGS. 8 and 9 are not meant to be drawn to scale.

As will be further described herein, capacitor structures 812 may be radiation blocking MIM capacitors or other radiation-blocking capacitor structures that may be used for both a circuit purpose in addition to blocking radiation from contacting circuitry layers 814a so as to prevent damage or undesirable effects when unblocked light strikes light sensitive circuitry in layers 814a, e.g., such as current leakage problems due to currents induced in underlying analog circuitry by a photoelectric effect, erasure of underlying FLASH memory circuitry, etc. Advantageously, significant supply bypass capacitance and noise reduction may be gained "for free" in one exemplary embodiment when using such radiation blocking capacitors.

In the illustrated embodiment of FIG. 8, the area of radiation-blocking capacitor structures 812 does not extend to cover all of those areas of underlying digital and/or analog circuitry layers 814a that are aligned beneath the overlying opaque top of package 801. Rather, areas of light sensitive digital or analog circuitry 814b may be formed in the uppermost layers within those peripheral areas lying underneath the package top since these peripheral areas are protected from radiation by the radiation-opaque package top. However, it is alternatively possible in another embodiment that radiation-blocking capacitor structures 812 may extend completely to the peripheral edges of the uppermost layers so as to cover all of underlying digital and/or analog circuitry layers 814a.

Still referring to FIG. 8, an opening 802 (e.g., about 1 millimeter deep) is defined in package 801 down to silicon and overlying capacitive sensor circuitry area 810 to allow ambient gases such as air to enter and interact with capacitive sensor circuitry area 810. As shown, opening 802 optionally has dimensions (e.g., diameter) greater than the outside dimensions or outer areal boundary 902 of capacitive sensor circuitry area 810. In this regard, opening 802 may be oversized relative to capacitive sensor circuitry area 810 in order to allow for combined package hole placement uncertainty together with circuitry placement uncertainty. For example, given an uncertainty of 150 microns for placement of opening 802 in package 801, and an uncertainty for placement of sensor system circuitry 820 within package 801, a combined uncertainty of 300 microns exists for alignment of opening 802 with capacitive sensor circuitry area 810. Thus, the dimensions (e.g., diameter) of opening 802 may be defined to be 300 microns larger than the outer dimensional boundary 902 (e.g., diameter) of capacitive sensor circuitry 810 to ensure that that capacitive sensor circuitry 810 is placed entirely within the boundary of opening 802 for optimal exposure to ambient gases. Thus, given a sensor boundary 902 of about 650 microns across and a combined placement uncertainty of about 300 microns, a package opening 802 of at least 950 microns across may be provided. As shown in FIG. 8 opening 802 is defined in radiation-opaque package 801 over both capacitive sensor circuitry area 810 and radiation-blocking capacitor structures 812, as well as over portions of the digital and/or analog circuitry layers 814a that underlie each of capacitive sensor circuitry area 810 and radiation-blocking capacitor structures 812. In this regard, radiation impinging from above package 801 may enter opening 802 and would otherwise penetrate to these underlying portions of the digital and/or analog circuitry layers 814a that lie beneath opening 802 if not blocked by capacitive sensor circuitry area 810 and radiation-blocking capacitor structures 812.

Figure 12:
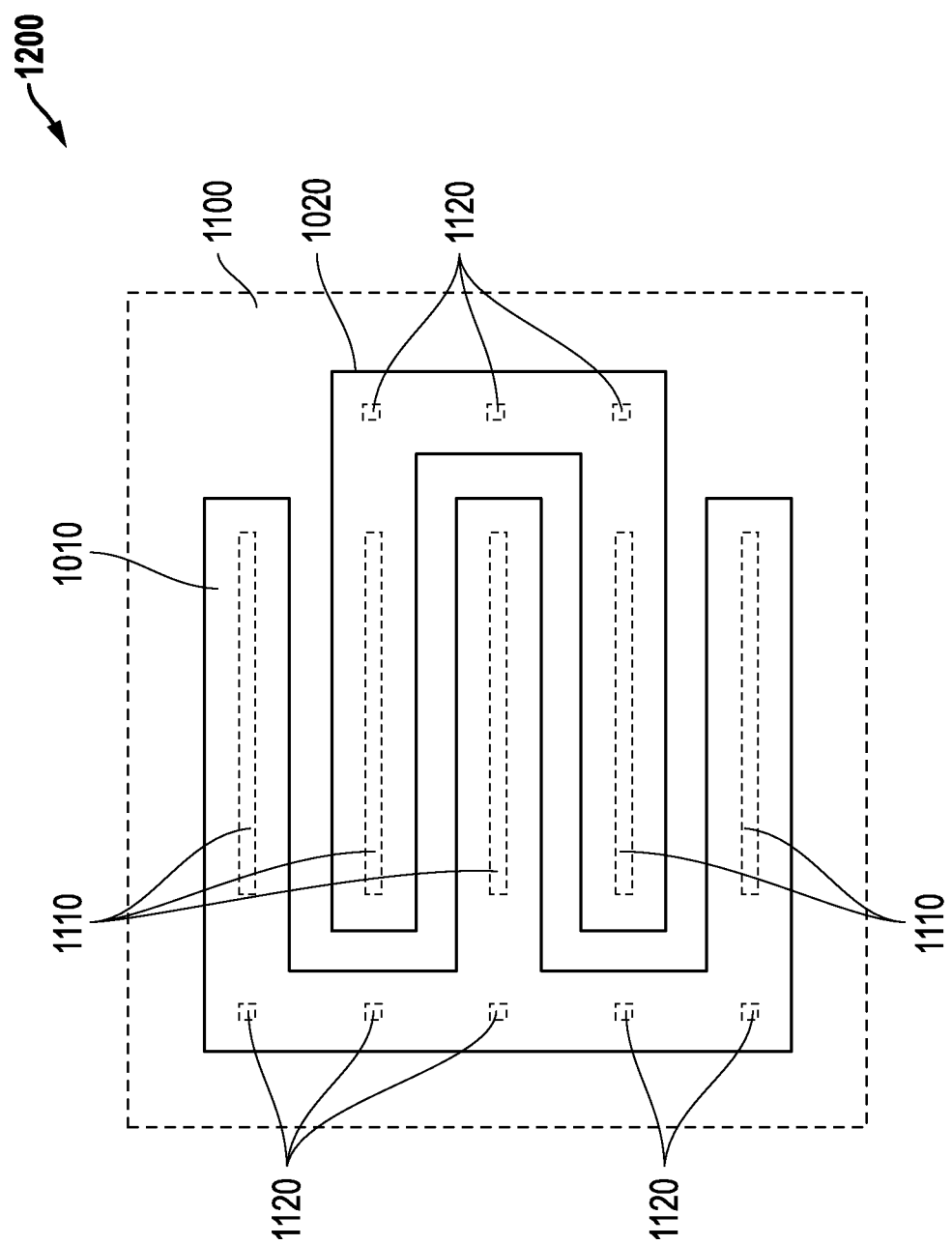
FIG. 12 illustrates a stacked structure of capacitor plates and a radiation-blocking shield according to one exemplary embodiment disclosed herein.

FIG. 9 is a partial overhead view of packaged integrated circuit device 800 of FIG. 8, showing the relationship between boundary of opening 802 and each of capacitive sensor circuitry area 810 and the surrounding other capacitor structure area 812. As may be seen from FIGS. 8 and 9, incident radiation that impinges on upper surface of package 801 will enter opening 802 and contact either capacitive sensor circuitry area 810 or surrounding other capacitor structure area 812. By configuring the overlying capacitor electrodes and underlying ground planes (e.g., see FIGS. 2A and 2B) of capacitive sensor circuitry area 810 as respective non-continuous opaque layer structures unit cells according to one or more of the radiation blocking relationships of FIGS. 5-7, any radiation, such as visible light, that strikes capacitive sensor circuitry area 810 may be blocked from penetrating to underlying active circuitry 814a. FIGS. 10-12 illustrate one exemplary embodiment of such a configuration.

Still referring to the exemplary embodiment of FIG. 9, radiation blocking structures are optionally provided in the surrounding other capacitor structure area 812 to also block other radiation that falls in the annular area between boundaries 802 and 902 from penetrating to underlying active circuitry 814. Such radiation blocking structures may be configured in any suitable manner to block one or more types of radiation according to the relationships described and illustrated in relation to FIGS. 5-7. In one particular embodiment, such radiation-blocking structures may be configured as metal-insulator-metal ("MIM") capacitor structures such as those described in relation to FIGS. 13-15 herein. However, it will be understood that radiation blocking structures may alternatively be any other type of circuitry components and/or opaque layer structures configured to block penetration of one or more types of radiation according to the relationships of FIGS. 5-7.

FIG. 10 illustrates a first metal capacitor plate 1010 and a second metal capacitor plate 1020 that may be provided in an overlying semiconductor device layer, such as layer 506 of FIGS. 5-7 to form the interdigitated finger electrodes for a capacitive sensor structure 1000 such as described and illustrated in relation to FIG. 2A or 2B. FIG. 11 illustrates a metal radiation blocking shield 1100 that may be provided in an underlying semiconductor device layer, such as layer 502 of FIGS. 5-7, e.g., to form a ground plane beneath the finger electrodes of a capacitive sensor structure of FIG. 2A or 2B. As shown in FIG. 10, metal radiation blocking shield 1100 has openings 1110 and 1120 defined therein for purposes of meeting metal width spacing rules, e.g., to ensure that that no areas of metal having dimensions greater than 25 microns×25 microns exists in a given layer without having a stress relief opening defined therein. It will be understood that placement of such openings may also be selected, in part, to achieve symmetry of the openings within the area of a given metal layer. FIG. 12 illustrates a stacked structure 1200 in which the overlying interdigitated finger electrodes for capacitive sensor structure are aligned with the underlying openings of the metal radiation blocking shield 1100 such that complete blocking of overhead-impinging radiation is achieved by the stacked structure 1200. It will be understood that FIGS. 10-11 are illustrative only, and that the number of overlying interdigitated finger electrodes and corresponding numbers of underlying openings may vary, and in one case may be much larger.

Figure 13:
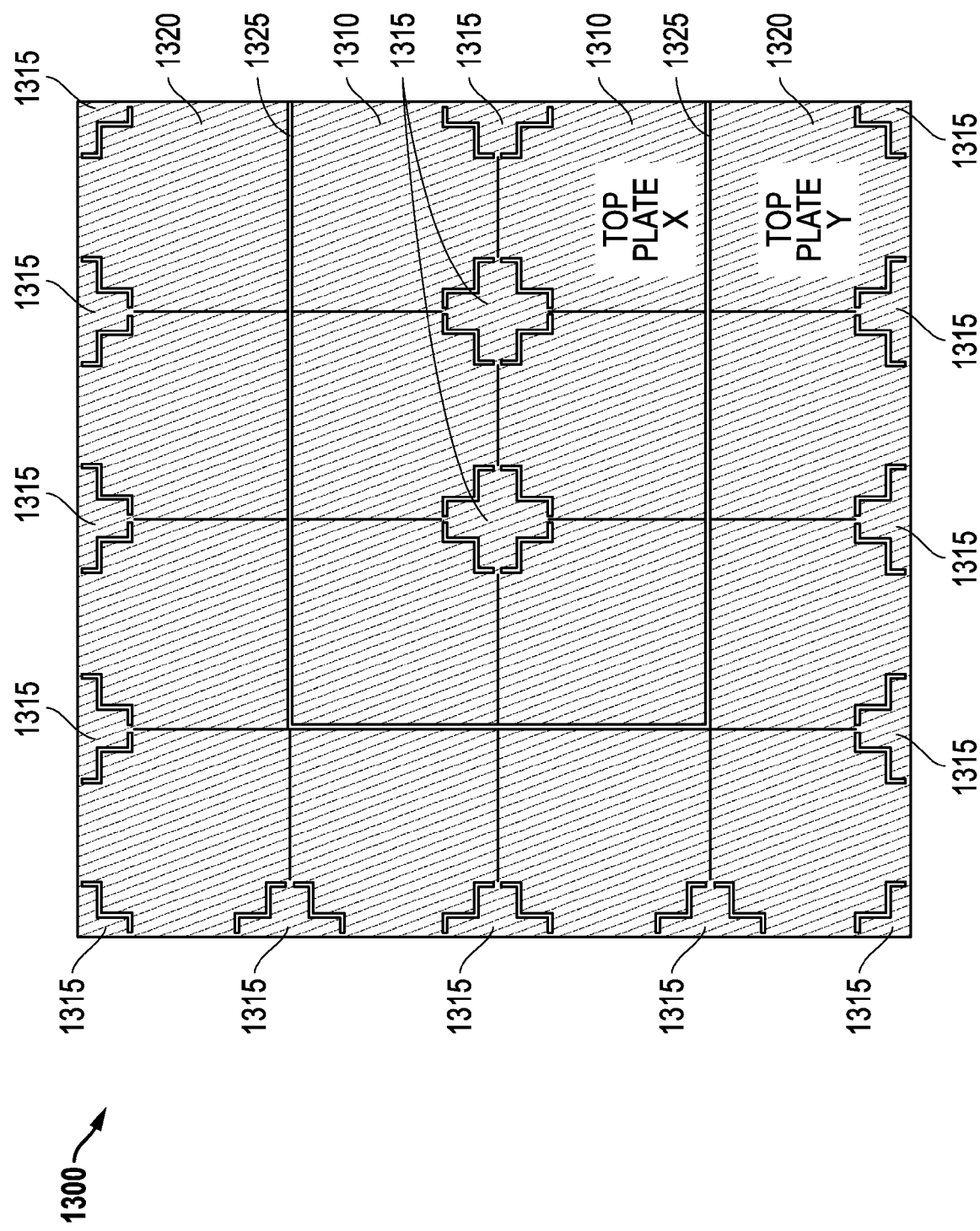
FIG. 13 illustrates a metal structure section of an overlying semiconductor device layer according to one exemplary embodiment disclosed herein.

FIG. 13 illustrates a section of top metal capacitor plates 1310 and 1320 that may be provided in the metal structure 1300 of an overlying semiconductor device layer, such as layer 506 of FIGS. 5-7 to form two adjacent top capacitor plates for two respective different MIM capacitors "X" and "Y" that are separated by an elongated non-metal capacitor plate separator space 1325 that divides the metal structure 1300 to create two separate plates 1310 and 1320. As shown, plus-shaped metal sections 1315 may each be formed in metal structure 1300 by a surrounding open (non-metal) boundary space defined in the metal of the layer to meet metal width spacing rules. Each of the metal sections 1315 may be conductively tied by a thin metal strip to its surrounding capacitor plate to prevent floating.

Figure 14:
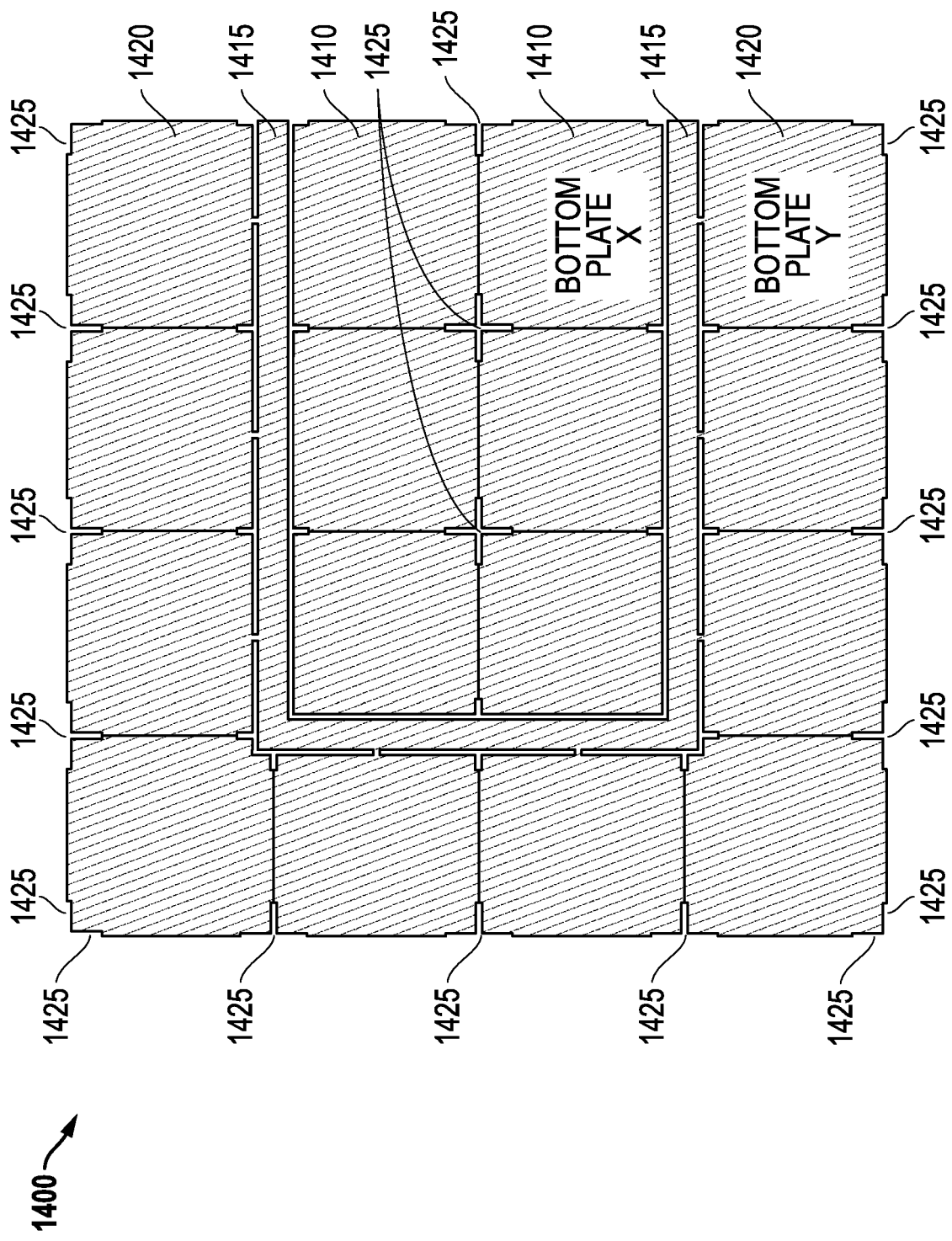
FIG. 14 illustrates a metal structure section of an underlying semiconductor device layer according to one exemplary embodiment disclosed herein.

FIG. 14 illustrates a section of bottom metal capacitor plates 1410 and 1420 that may be provided in the metal structure 1400 of an underlying semiconductor device layer, such as layer 502 of FIGS. 5-7 to form two separate adjacent bottom capacitor plates 1410 and 1420 that correspond to the two separate top plates 1310 and 1320 for the two respective different MIM capacitors "X" and "Y". As shown in FIG. 14, an elongated metal blocking strip 1415 may be formed by adjacent parallel non-metal boundary spaces defined in the metal of the layer to meet metal width spacing rules, and may be shaped to correspond to shape and location of overlying elongated non-metal capacitor plate separator space 1325. Metal strip 1415 may be conductively tied by a thin metal strip to one of the surrounding capacitor plates 1410 or 1420 to prevent floating. As further shown, plus-shaped openings 1425 in metal structure 1400 may be defined in each of capacitor plates 1410 and 1420 to meet metal width spacing rules, and may be shaped to correspond to shape and location of overlying plus-shaped metal sections 1315.

Figure 15:
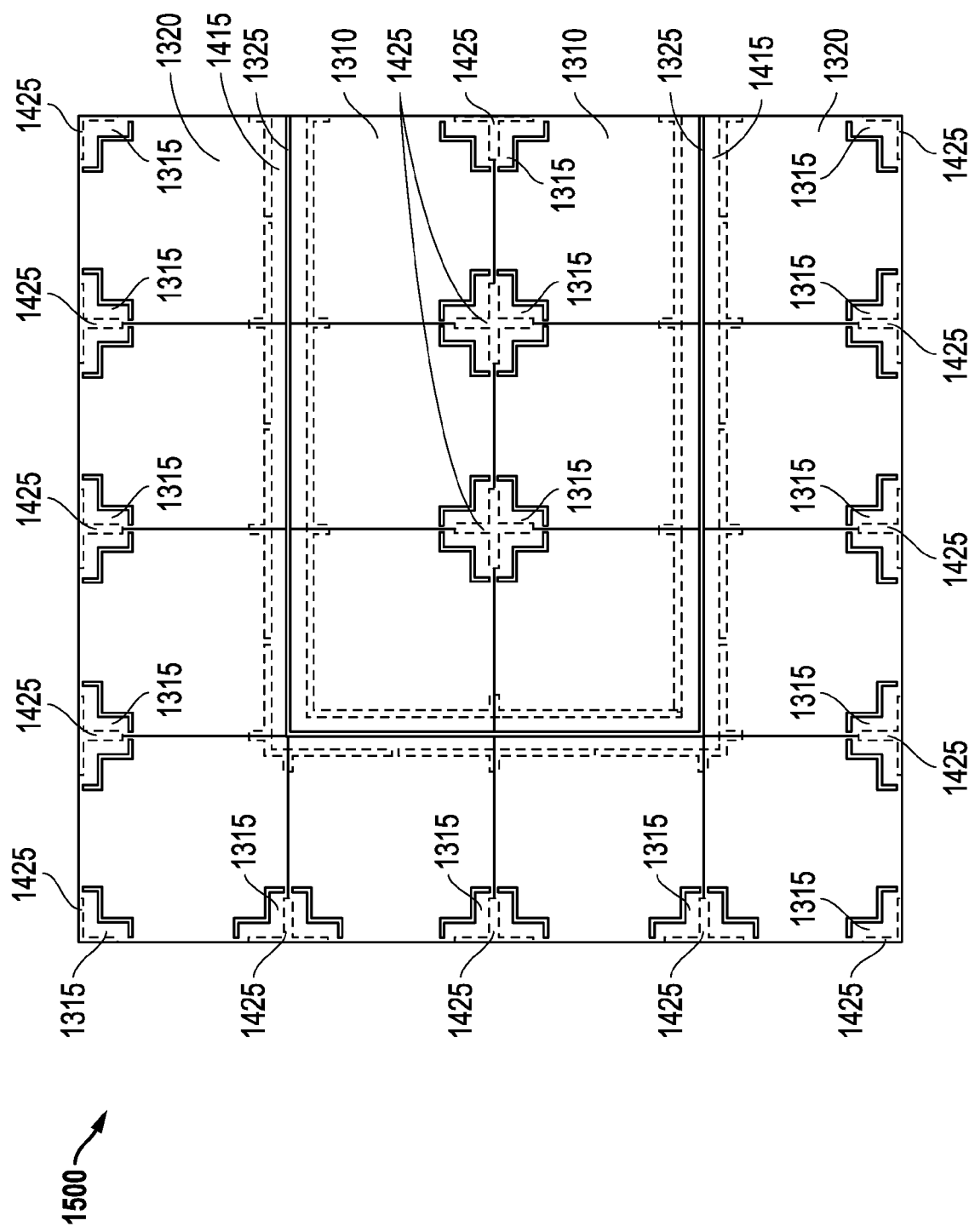
FIG. 15 illustrates a section of a stacked structure an overlying semiconductor device and an underlying semiconductor device layer according to one exemplary embodiment disclosed herein.

FIG. 15 illustrates a section of a stacked structure 1500 in which the overlying metal structure 1300 of FIG. 13 is aligned with the underlying metal structure 1400 of FIG. 14 such that complete blocking of overhead-impinging radiation is achieved by the resulting stacked structure 1500. As shown in FIG. 15, elongated radiation-blocking strip 1415 aligns with the shape and location of overlying elongated non-metal capacitor plate separator space 1325 so as to completely block penetration of radiation through the stacked metal structures, e.g., according to the relationships described in relation to FIGS. 5-7 herein. Similarly, each of overlying plus-shaped metal sections 1315 aligns with the shape and location of a given underlying plus-shaped openings 1425 so as to completely block penetration of radiation through the stacked metal structures, e.g., according to the relationships described in relation to FIGS. 5-7 herein. It will be understood that the particular shapes of plus-shaped metal sections 1315, plus-shaped openings 1425, elongated metal blocking strip 1415 and elongated non-metal capacitor plate separator space 1325 are exemplary only, and that other shapes and variety of shapes may be employed as needed or desired to fit particular radiation-blocking applications. Moreover, it will be understood that only one MIM capacitor may be formed by stacked metal layers (i.e., rather than the illustrated separate "X" and "Y" capacitors) using the techniques and structures disclosed herein, or that more than two capacitors may be alternatively formed by stacked metal layers using the techniques and structures disclosed herein.

Figure 16:
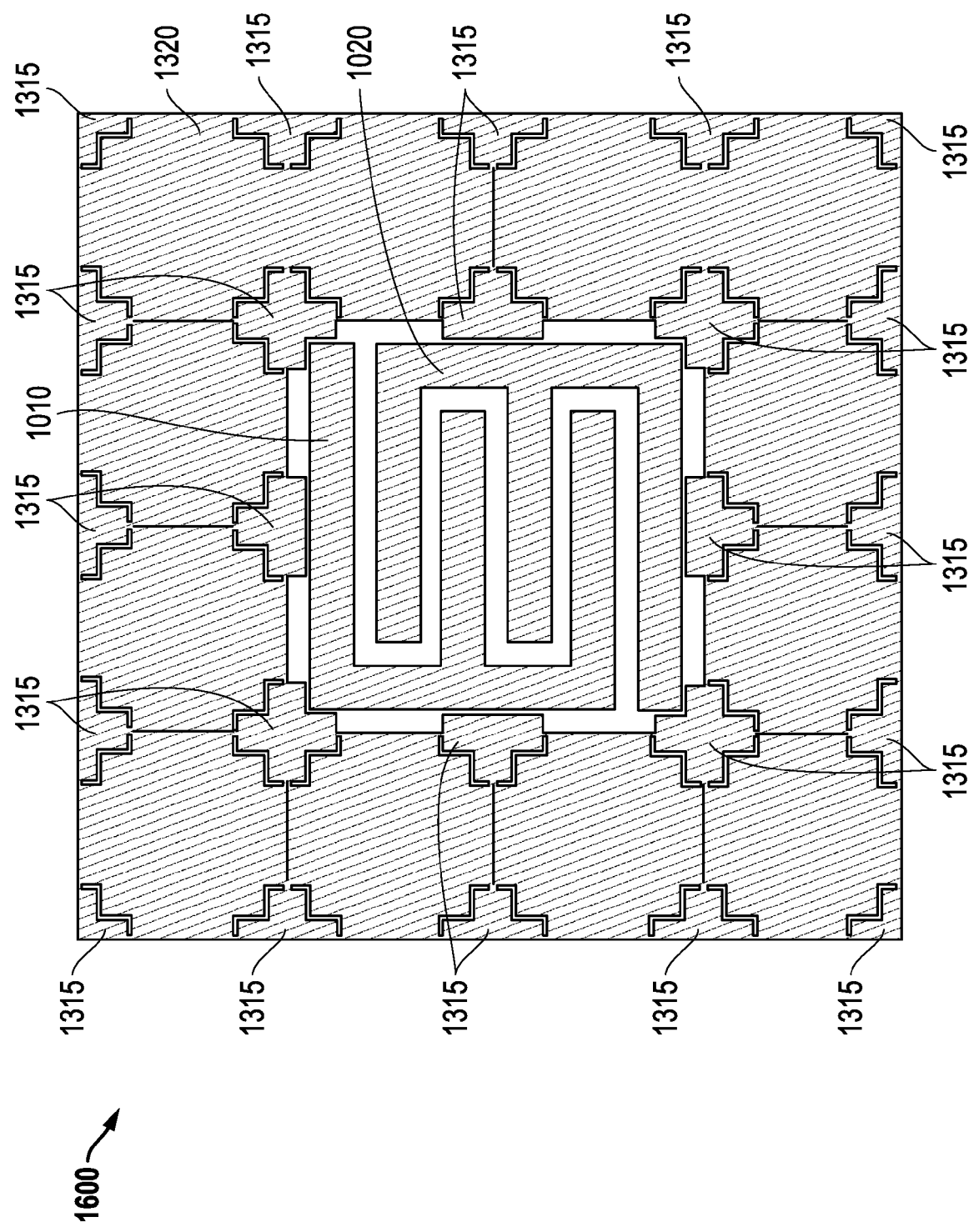
FIG. 16 illustrates a metal structure section of an overlying semiconductor device layer according to one exemplary embodiment disclosed herein.
Figure 17:
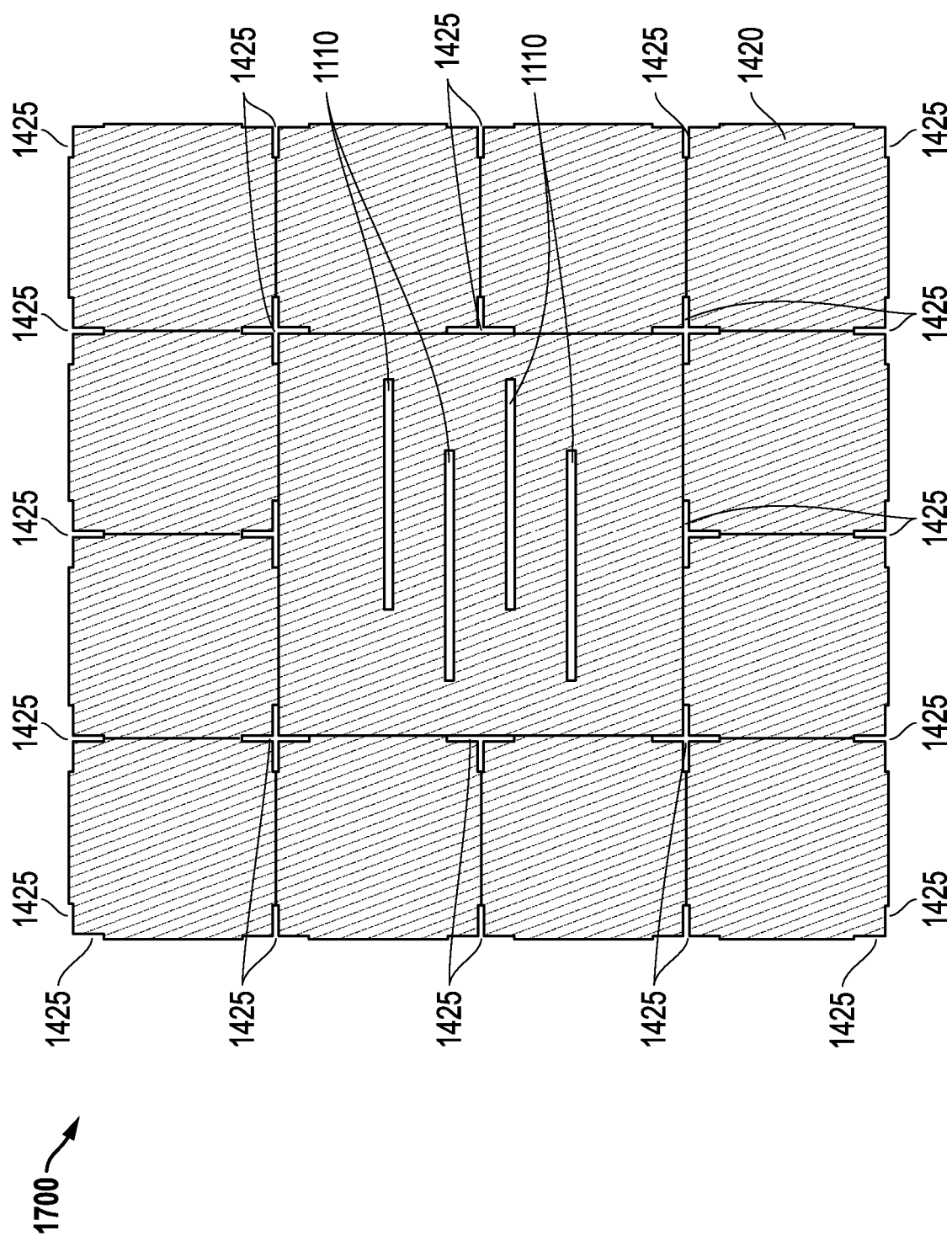
FIG. 17 illustrates a metal structure section of an underlying semiconductor device layer according to one exemplary embodiment disclosed herein.
Figure 18:
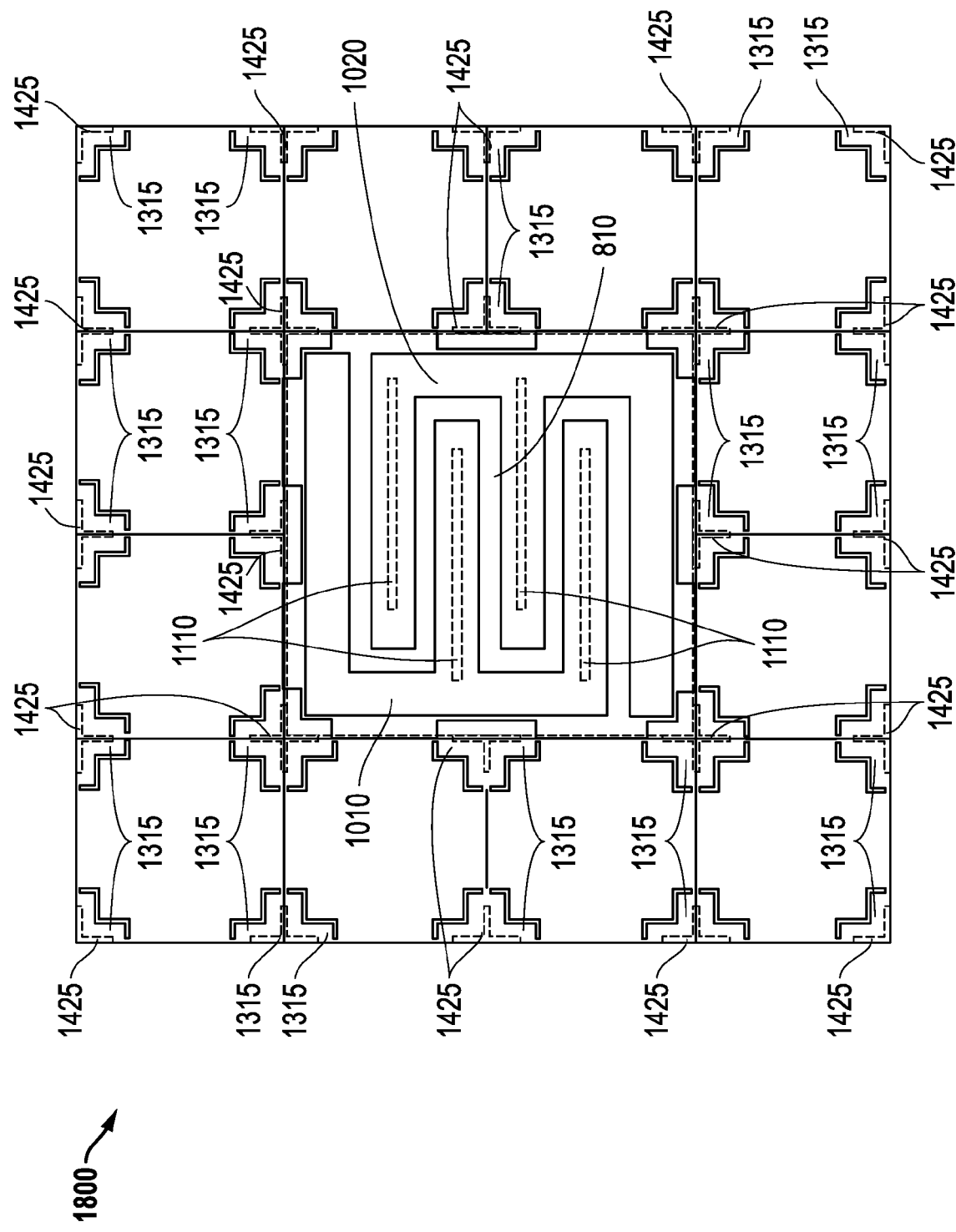
FIG. 18 illustrates a section of a stacked structure an overlying semiconductor device and an underlying semiconductor device layer according to one exemplary embodiment disclosed herein.

FIGS. 16-18 illustrate and exemplary embodiment in which an example radiation-blocking six-finger capacitive sensor structure 810 is surrounded by other radiation-blocking capacitor structure circuitry 812 (e.g., bypass capacitor or decoupling capacitor circuitry) such as described in relation to FIGS. 8 and 9. It will be understood that capacitive sensor structure 810 may be replicated many times to create a much larger sensor area with many more interdigitated finger capacitor electrodes than shown and that other capacitive sensor structure 810 may extend much further outward, e.g., to implement a packaged integrated circuit device 800 of the scale such as illustrated and descried in relation to FIGS. 8 and 9.

In particular, FIG. 16 illustrates a section of a metal structure 1300 that includes a single top metal capacitor plate 1320 of an overlying semiconductor device layer, such as layer 506 of FIGS. 5-7, that is configured with plus-shaped metal sections 1315 in a manner and for the same purposes as previously described. Metal structure 1300 also includes a first metal capacitor plate 1010 and a second metal capacitor plate 1020 that are separated from the surrounding capacitor plate 1320 to form the interdigitated finger electrodes for a capacitive sensor structure such as described and illustrated in relation to FIG. 2A or 2B.

FIG. 17 illustrates a section of a metal structure 1400 that includes a single bottom metal capacitor plate 1420 of an underlying semiconductor device layer, such as layer 502 of FIGS. 5-7 that is configured with plus-shaped openings 1425 therein in a manner and for the same purposes as previously described. Metal structure 1400 also includes a metal radiation blocking shield configured to underlie the capacitive sensor structure of metal structure 1300. As with metal radiation blocking shield 1100 of FIG. 11, openings 1110 are defined in the radiation blocking shield of metal structure 1400 in the same manner as previously described. Further, in this embodiment metal radiation blocking shield forms part of single bottom metal capacitor plate 1420 as shown.

FIG. 18 illustrates a section of a stacked structure 1800 in which the overlying metal structure 1600 of FIG. 16 is aligned with the underlying metal structure 1700 of FIG. 17 to form a capacitive sensor circuitry area 810 surrounded by other radiation-blocking capacitor structures 812 such that complete blocking of overhead-impinging radiation is achieved by the resulting stacked structure 1800. It is noted that for illustration purposes the structures of FIGS. 10-18 are not meant to be drawn to scale.

Further modifications and alternative embodiments of this invention will be apparent to those skilled in the art in view of this description. It will be recognized, therefore, that the present invention is not limited by these example arrangements. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the implementations and architectures. For example, equivalent elements may be substituted for those illustrated and described herein and certain features of the invention may be utilized independently of the use of other features, all as would be apparent to one skilled in the art after having the benefit of this description of the invention.

The invention claimed is:

1. A multi-layer semiconductor device, comprising:
a first device layer including one or more non-continuous first radiation-opaque layer structures defining radiation transmissive areas in the first device layer; and
a second device layer underlying the first device layer, the second device layer including one or more non-continuous second radiation-opaque layer structures defining radiation transmissive areas in the second device layer;
where the first non-continuous opaque structures of the first device layer are cooperatively spaced in overlapping relationship with the second non-continuous opaque structures of the second device layer to form a continuous barrier that completely blocks all radiation that impinges on the first device layer from above the semiconductor device from penetrating through the combination of the first and second device layers of the multi-layer structure;
where the semiconductor device further comprises a third device layer disposed between the first and second device layers, the third device layer comprising radiation-transmissive dielectric material; and where each of the first and second non-continuous opaque structures comprise non-continuous metal structures; and
where the semiconductor comprises a gas sensor device; where the first non-continuous opaque structures of the first device layer comprise sensor electrodes for the gas sensor device; and where the second non-continuous opaque structures of the second device layer comprise ground planes.

2. The semiconductor device of claim 1, where the first non-continuous opaque structures of the first device layer together comprise at least one top plate of a metal-insulator-metal (MIM) capacitor with one or more radiation-transmissive openings defined therein; where the second non-continuous opaque structures of the second device layer together comprise at least one bottom plate of the MIM capacitor with one or more radiation-transmissive openings defined therein.

3. The semiconductor device of claim 1, where the blocked electromagnetic radiation comprises at least one of sunlight, artificial light, ultraviolet radiation, infrared radiation, or a combination thereof.

4. A multi-layer semiconductor device, comprising:
a first device layer including one or more non-continuous first radiation-opaque layer structures defining radiation transmissive areas in the first device layer; and
a second device layer underlying the first device layer, the second device layer including one or more non-continuous second radiation-opaque layer structures defining radiation transmissive areas in the second device layer;
where the first non-continuous opaque structures of the first device layer are cooperatively spaced in overlapping relationship with the second non-continuous opaque structures of the second device layer to form a continuous barrier that completely blocks all radiation that impinges on the first device layer from above the semiconductor device from penetrating through the combination of the first and second device layers of the multi-layer structure; and
where the semiconductor device further comprises one or more additional device layers underlying the second device layer, the additional device layers having radiation-sensitive active circuitry formed therein; where the first non-continuous opaque structures of the first device layer are cooperatively spaced in overlapping relationship with the second non-continuous opaque structures of the second device layer to form a continuous barrier that completely blocks all radiation that impinges on the first device layer from above the semiconductor device from penetrating further into the semiconductor device to the underlying radiation-sensitive circuitry.

5. The semiconductor device of claim 4, where the semiconductor comprises a gas sensor device; where the first non-continuous opaque structures of the first device layer comprise sensor electrodes for the gas sensor device; and where the second non-continuous opaque structures of the second device layer comprise ground planes.

6. The semiconductor device of claim 5, further comprising a radiation-opaque package surrounding the multiple device layers of the gas sensor device with a radiation-transmissive opening being defined in the package over the gas sensor electrodes and underlying ground planes and radiation-sensitive circuitry, the opening being configured to expose the gas sensor electrodes to ambient conditions outside the package.

7. A capacitive gas sensor, comprising:
a gas sensitive material, the gas sensor configured to allow the exposure of the gas sensitive material to a gas;
first non-continuous radiation-opaque structures comprising spaced metal capacitor electrodes of a capacitive sensor cell provided in a first device layer, the capacitive sensor cell being electrically coupled to at least a portion of the gas sensitive material;
second non-continuous radiation-opaque structures comprising one or more metal non-continuous ground planes in a second device layer underlying the capacitor electrodes; and
lower level circuitry underlying the spaced metal capacitor electrodes and ground planes of the first and second device layers;
where the gas sensor is configured to utilize a detected capacitance between the electrodes of the capacitive sensor cell to obtain a gas sensor measurement; and
where the capacitor electrodes of the first device layer are cooperatively spaced in overlapping relationship with the non-continuous ground planes of the second device layer to block impinging light from further penetration into the lower level circuitry.

8. The gas sensor of claim 7, further comprising a third device layer disposed between the first and second device layers, the third device layer comprising radiation-transmissive dielectric material.

9. The gas sensor of claim 7, further comprising a radiation-opaque package surrounding the multiple device layers of the gas sensor with a radiation-transmissive opening being defined in the package over the spaced metal capacitor electrodes and underlying ground planes and lower level circuitry, the opening being configured to expose the spaced metal capacitor electrodes to ambient conditions outside the package.

10. The gas sensor of claim 7, where the first non-continuous opaque structures of the first device layer further comprise at least one top plate of a metal-insulator-metal (MIM) capacitor that is non-continuous with the spaced metal capacitor electrodes of the gas sensor and that defines one or more radiation transmissive areas in the first device layer; and where the second non-continuous opaque structures of the second device layer together comprise at least one bottom plate of the MIM capacitor defining one or more radiation transmissive areas in the second device layer.

11. The gas sensor of claim 10, further comprising a radiation-opaque package surrounding the multiple device layers of the gas sensor with a radiation-transmissive opening being defined in the package over the spaced metal capacitor electrodes and underlying ground planes and lower level circuitry; and where the radiation-transmissive opening is also defined in the package over at least a portion of the MIM capacitor and underlying lower level circuitry, the opening being configured to expose the spaced metal capacitor electrodes to ambient conditions outside the package.

12. A method of forming a multi-layer semiconductor device, the method comprising:
  providing a first device layer including one or more non-continuous first radiation-opaque layer structures defining radiation transmissive areas in the first device layer;
  providing a second device layer underlying the first device layer, the second device layer including one or more non-continuous second radiation-opaque layer structures defining radiation transmissive areas in the second device layer;
  configuring the first non-continuous opaque structures of the first device layer to be cooperatively spaced in overlapping relationship with the second non-continuous opaque structures of the second device layer to form a continuous barrier that completely blocks all radiation that impinges on the first device layer from above the semiconductor device from penetrating through the combination of the first and second device layers of the multi-layer structure; and
  providing a third device layer disposed between the first and second device layers, the third device layer comprising radiation-transmissive dielectric material; where the semiconductor comprises a gas sensor device; where the first non-continuous opaque structures of the first device layer comprise sensor electrodes for the gas sensor device; where the second non-continuous opaque structures of the second device layer comprise ground planes; and where each of the first and second non-continuous opaque structures comprise non-continuous metal structures.

13. The method of claim 12, where the first non-continuous opaque structures of the first device layer together comprise at least one top plate of a metal-insulator-metal (MIM) capacitor with one or more radiation-transmissive openings defined therein; where the second non-continuous opaque structures of the second device layer together comprise at least one bottom plate of the MIM capacitor with one or more radiation-transmissive openings defined therein.

14. A method of forming a multi-layer semiconductor device, the method comprising:
  providing a first device layer including one or more non-continuous first radiation-opaque layer structures defining radiation transmissive areas in the first device layer;
  providing a second device layer underlying the first device layer, the second device layer including one or more non-continuous second radiation-opaque layer structures defining radiation transmissive areas in the second device layer;
  configuring the first non-continuous opaque structures of the first device layer to be cooperatively spaced in overlapping relationship with the second non-continuous opaque structures of the second device layer to form a continuous barrier that completely blocks all radiation that impinges on the first device layer from above the semiconductor device from penetrating through the combination of the first and second device layers of the multi-layer structure; and
  providing one or more additional device layers underlying the second device layer, the additional device layers having radiation-sensitive active circuitry formed therein; where the first non-continuous opaque structures of the first device layer are cooperatively spaced in overlapping relationship with the second non-continuous opaque structures of the second device layer to form a continuous barrier that completely blocks all radiation that impinges on the first device layer from above the semiconductor device from penetrating further into the semiconductor device to the underlying radiation-sensitive circuitry.

15. A method of forming a capacitive gas sensor, comprising:
  providing a gas sensitive material, the gas sensor provided to allow the exposure of the gas sensitive material to a gas;
  providing first non-continuous radiation-opaque structures comprising spaced metal capacitor electrodes in a first device layer of a capacitive sensor cell, the capacitive sensor cell being electrically coupled to at least a portion of the gas sensitive material;
  providing second non-continuous radiation-opaque structures comprising one or more metal non-continuous metal ground planes in a second device layer underlying the capacitor electrodes;
  providing lower level circuitry underlying the spaced metal capacitor electrodes and ground planes of the first and second device layers;
  configuring the gas senor to utilize a detected capacitance between the electrodes of the capacitive sensor cell to obtain a gas sensor measurement; and
  configuring the capacitor electrodes of the first device layer to be cooperatively spaced in overlapping relationship with the non-continuous ground planes of the second device layer to block impinging light from further penetration into the lower level circuitry.

16. The method of claim 15, further comprising providing a third device layer disposed between the first and second device layers, the third device layer comprising radiation-transmissive dielectric material.

17. The method of claim 15, further comprising providing a radiation-opaque package surrounding the multiple device layers of the gas sensor with a radiation-transmissive opening being defined in the package over the spaced metal capacitor electrodes and underlying ground planes and lower level circuitry, the opening being configured to expose the spaced metal capacitor electrodes to ambient conditions outside the package.

18. The method of claim 15, where the first non-continuous opaque structures of the first device layer further comprise at least one top plate of a metal-insulator-metal (MIM) capacitor that is non-continuous with the spaced metal capacitor electrodes of the gas sensor and that defines one or more radiation transmissive areas in the first device layer; and where the second non-continuous opaque structures of the second device layer together comprise at least one bottom plate of the MIM capacitor defining one or more radiation transmissive areas in the second device layer.

19. The method of claim 18, further comprising providing a radiation-opaque package surrounding the multiple device layers of the gas sensor with a radiation-transmissive opening being defined in the package over the spaced metal capacitor electrodes and underlying ground planes and lower level circuitry, the radiation-transmissive opening also being defined in the package over at least a portion of the MIM capacitor and underlying lower level circuitry, the opening being configured to expose the spaced metal capacitor electrodes to ambient conditions outside the package.

\* \* \* \* \*